United States Patent
Burn et al.

(10) Patent No.: US 10,151,700 B2
(45) Date of Patent: Dec. 11, 2018

(54) METHOD FOR THE DETECTION OF ANALYTES VIA LUMINESCENCE QUENCHING

(71) Applicant: The University of Queensland, St. Lucia, Queensland (AU)

(72) Inventors: Paul Leslie Burn, St. Lucia (AU); Paul Meredith, St. Lucia (AU); Paul Edward Shaw, St. Lucia (AU)

(73) Assignee: THE UNIVERSITY OF QUEENSLAND, Queensland (AU)

( * ) Notice: Subject to any disclaimer, the term of this patent is extended or adjusted under 35 U.S.C. 154(b) by 0 days.

(21) Appl. No.: 15/829,911

(22) Filed: Dec. 2, 2017

(65) Prior Publication Data
US 2018/0100801 A1   Apr. 12, 2018

Related U.S. Application Data

(63) Continuation of application No. 14/649,780, filed as application No. PCT/AU2013/001410 on Dec. 4, 2013.

(30) Foreign Application Priority Data

Dec. 4, 2012  (AU) ................................ 2012905287

(51) Int. Cl.
*G01N 21/64* (2006.01)
*G01N 33/00* (2006.01)
(Continued)

(52) U.S. Cl.
CPC .......... *G01N 21/643* (2013.01); *C07C 211/54* (2013.01); *C07D 333/20* (2013.01);
(Continued)

(58) Field of Classification Search
CPC ................ C07C 211/54; C07D 333/20; G01N 2021/0346; G01N 2021/6432;
(Continued)

(56) References Cited

U.S. PATENT DOCUMENTS

2008/0039581 A1* 2/2008 Brown .................. C07C 211/54
524/796
2008/0242870 A1* 10/2008 Meador ................ C07D 487/04
548/417

(Continued)

FOREIGN PATENT DOCUMENTS

CN  101891642 A   11/2010
EP  0 128 723 A2   12/1984
(Continued)

OTHER PUBLICATIONS

Richardson, S., et al., "Chemosensing of 1,4-dinitrobenzene using bisfluorene dendrimer distributed feedbackasers," Applied Physics Letters, vol. 95, 2009, pp. 063305-1-063305-3.*
(Continued)

*Primary Examiner* — Jennifer Wecker
(74) *Attorney, Agent, or Firm* — Nixon & Vanderhye P.C.

(57) ABSTRACT

A sensing element for use in the detection of an analyte based on a luminescent response, the sensing element comprising a luminescent triaryl amine compound provided as a coating on a substrate.

18 Claims, 13 Drawing Sheets

(51) Int. Cl.
   *G01N 33/52* (2006.01)
   *C07C 211/54* (2006.01)
   *C07D 333/20* (2006.01)
   *G01N 21/03* (2006.01)

(52) U.S. Cl.
   CPC ....... *G01N 21/645* (2013.01); *G01N 21/6408* (2013.01); *G01N 33/0057* (2013.01); *G01N 33/52* (2013.01); *G01N 2021/0346* (2013.01); *G01N 2021/6432* (2013.01); *G01N 2021/6482* (2013.01)

(58) Field of Classification Search
   CPC ....... G01N 2021/6482; G01N 21/6408; G01N 21/643; G01N 21/645; G01N 33/0057; G01N 33/52
   See application file for complete search history.

(56) References Cited

U.S. PATENT DOCUMENTS

| | | | |
|---|---|---|---|
| 2008/0248330 A1* | 10/2008 | Joo | C07C 211/54 428/704 |
| 2010/0210029 A1* | 8/2010 | Meinhart | G01N 21/05 436/168 |
| 2011/0082354 A1 | 4/2011 | Ohnishi | |

FOREIGN PATENT DOCUMENTS

| | | |
|---|---|---|
| EP | 0 175 585 A1 | 3/1986 |
| EP | 1 887 344 A1 | 2/2008 |
| JP | 59/019843 A | 2/1984 |
| JP | 60-036963 A | 2/1985 |
| JP | 61-089528 A | 5/1986 |
| JP | 09-503866 A | 4/1997 |
| JP | 2001-232320 A | 11/2011 |
| WO | 95/010766 A1 | 4/1995 |
| WO | 2006/126683 A1 | 11/2006 |

OTHER PUBLICATIONS

Olley, David A., et al., "Explosive Sensing with Fluorescent Dendrimers: The Role of Collisional Quenching," Chem_Mater., vol. 23, No. 3, 2011, pp. 789-794.*

Olley, David A., et al., "Explosive Sensing with Fluorescent Dendrimers: The Role of Collisional Quenching," Chem_Mater., vol. 23, No. 3, 2011, pp. 789-794 (Year: 2011).*

English Translation of Jan. 4, 2017 Notification of the First Office Action issued in Chinese Patent Application No. 201380071554.4.

English Translation of Oct. 30, 2017 Notification of the Second Office Action issued in Chinese Patent Application No. 201380071554.4.

Hirade et al., "Small molecular organic photovoltaic cells with exciton blocking layer at anode interface for improved device performance," Applied Physics Letters, vol. 99, 2011, pp. 153302-1-153302-3.

Jan. 20, 2017 First Examination Report issued in Australian Application No. 2013354896.

Jun. 1, 2016 Extended European Search Report issued in European Application No. 13859713.3.

Jun. 20, 2017 Communication pursuant to Article 94(3) EPC issued in European Application No. 13 859 713.3.

Lana-Villarreal et al., "Characterization and Polymerization of Thienylphenyl and Selenylphenyl Amines and Their Interaction with CdSe Quantum Dots," ChemPhysChem, vol. 12, 2011, pp. 1155-1164.

Oct. 5, 2017 Notice of Reasons for Rejection issued in Japanese Patent Application No. 2015545600 (with translation).

Olley et al., "Explosive Sensing with Fluorescent Dendrimers: The Role of Collisional Quenching," Chemistry of Materials, 2011, vol. 23, No. 3, pp. 789-794 (XP055254593).

Richardson et al., "Chemosensing of 1,4-dinitrobenzene using bisfluorene dendrimer distributed feedback lasers," Applied Physics Letters, vol. 95, 2009, pp. 063305-1-063305-3.

Roquet et al., "Triphenylamine-Thienylenevinylene Hybrid Systems with Internal Charge Transfer as Donor Materials for Heterojunction Solar Cells," J. Am. Chem. Soc., vol. 128, No. 10, 2006, pp. 3459-3466 (XP-002397900).

Satoh et al., "Metal-Assembling Dendrimers with a Triarylamine Core and Their Application to a Dye-Sensitized Solar Cell," J. Am. Chem. Soc., vol. 127, No. 37, 2005, pp. 13030-13038.

Vamvounis et al., "Design protocols in triarylamine cored dendrimer-based explosive sensors," J. Mater. Chem. C, vol. 1, 2013, pp. 1322-1329.

Wren et al., "The effect of dendronisation of arylamine centred chromophores on field effect transistor performance," Polym. Chem., vol. 1, 2010, pp. 1117-1126.

Dated Jul. 18, 2018 Notification of the Third Office Action issued in Chinese Application No. 201380071554.4 (only English-language translation).

Zhao et al., "Luminescent aggregates of a starburst silole-triphenylamine adduct for sensitive explosive detection," Dyes and Pigments, Elsevier, vol. 91, No. 2, Mar. 15, 2011, pp. 258-263.

Zhao, "The design synthesis and properties of highly emissive organic solids," CMFD, Engineering Science and Technology, vol. I, No. 4, Apr. 15, 2012, pp. 3-4 (with English-language Abstract).

* cited by examiner

METHOD FOR THE DETECTION OF ANALYTES VIA LUMINESCENCE QUENCHING

This application is a continuation of U.S. patent application Ser. No. 14/649,780 filed 4 Jun. 2015, which is the U.S. national phase of International Application No. PCT/AU2013/001410 filed 4 Dec. 2013, which designated the U.S. and claims priority to AU Patent Application No. 2012905287 filed 4 Dec. 2012, the entire contents of each of which are hereby incorporated by reference.

FIELD OF THE INVENTION

The present invention relates to the detection of analytes, in particular explosives and explosives-related materials.

BACKGROUND TO THE INVENTION

The ability to reliably detect a specific compound even at low concentrations is a continuing challenge, and there is the on-going need to provide new methodologies and devices to do this. The detection of explosives and explosives-related compounds that are commonly used in terrorist attacks and war zones is a particularly pressing need. Although there is often talk of dirty bombs, biological and nuclear terrorism, and improvised explosive devices (IEDs) the majority of weapons still use nitroaromatic and nitroaliphatic materials either as the explosive, detonator, accelerant or taggant. There remains therefore a clear need to be able to detect these materials with suitably high sensitivity and selectivity.

Many commercially available sensors rely on detection of secondary species that are produced when a target analyte (target molecule) is present in an environment. For example, in such sensors the target analyte may be decomposed by chemical reaction to produce another molecule that is itself then detected. This approach to detection is indirect in nature and while being sensitive can be somewhat inefficient due to the time taken from sampling to detection. Other detection methods require direct contact sampling. The disadvantage of these latter methods is that they are reliant on a specific area of a substrate where the explosive analyte is present to be sampled, for example, swabbed.

An approach for direct detection of a target analyte relies on the use of luminescent compounds. When some compounds are exposed to light of a certain wavelength, they absorb the light (photoexcitation) and emit light of a different wavelength (luminescence, which can either be fluorescence or phosphorescence). This emitted light can be measured/detected. However, certain analyte molecules may also interact with the (excited) luminescent compound to cause an increase or decrease in the intensity of the emitted light. This change can also be detected and, as such, can be used to indicate the presence of the analyte molecules. Sensors embodying the luminescence quenching approach are commercially available. The sensing materials are comprised of thin films containing luminescent conjugated polymers. These sensors can demonstrate high sensitivity but there is scope for improvement in terms of selectivity, especially when the intention is to detect an explosives or explosive-related materials. False positives can occur since every-day products, such as cosmetics, coffee and solvents, can illicit the same qualitative decrease in luminescent intensity as explosives and explosive-related materials. This is a significant limitation on the usefulness of these existing conjugated polymer sensors.

Against this background it would be desirable to provide a sensor technology that does not suffer these drawbacks. It would be particularly desirable to provide a sensor technology that shows high sensitivity to key analytes, such as explosives and explosives-related materials, and that allows the presence of such key analytes to be identified by a characteristic response that per se is specific and selective for those analytes. In this way the presence of every-day chemicals would give a different response to that of the desired explosives and explosives-related materials.

SUMMARY OF THE INVENTION

In an embodiment the present invention provides a method of detecting an analyte, which method comprises:
(i) allowing a luminescent compound comprising a triaryl amine moiety to interact with the analyte and measuring the luminescent properties of the compound due to exposure to the analyte;
(ii) detecting a difference between the luminescent properties measured in step (i) and the luminescent properties of the compound prior to measurement of luminescent properties in step (i); and
(iii) determining whether the analyte is present based on the difference in luminescent properties detected in step (ii).

The present invention also provides a sensing element for use in the detection of an analyte based on a luminescent response, the sensing element comprising a luminescent compound comprising a triaryl amine moiety provided as a coating on a substrate. The sensing element is used in sensor devices that employ the methodology of the present invention.

The present invention also provides a sensor device for the detection of an analyte based on a change in the measured luminescence, the sensor device comprising a sensing element in accordance with the present invention. The sensor device employs the methodology of the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

BRIEF DISCUSSION OF THE DRAWINGS

Embodiments of the present invention are illustrated with reference to the accompanying drawings in which.

Figure 10A:
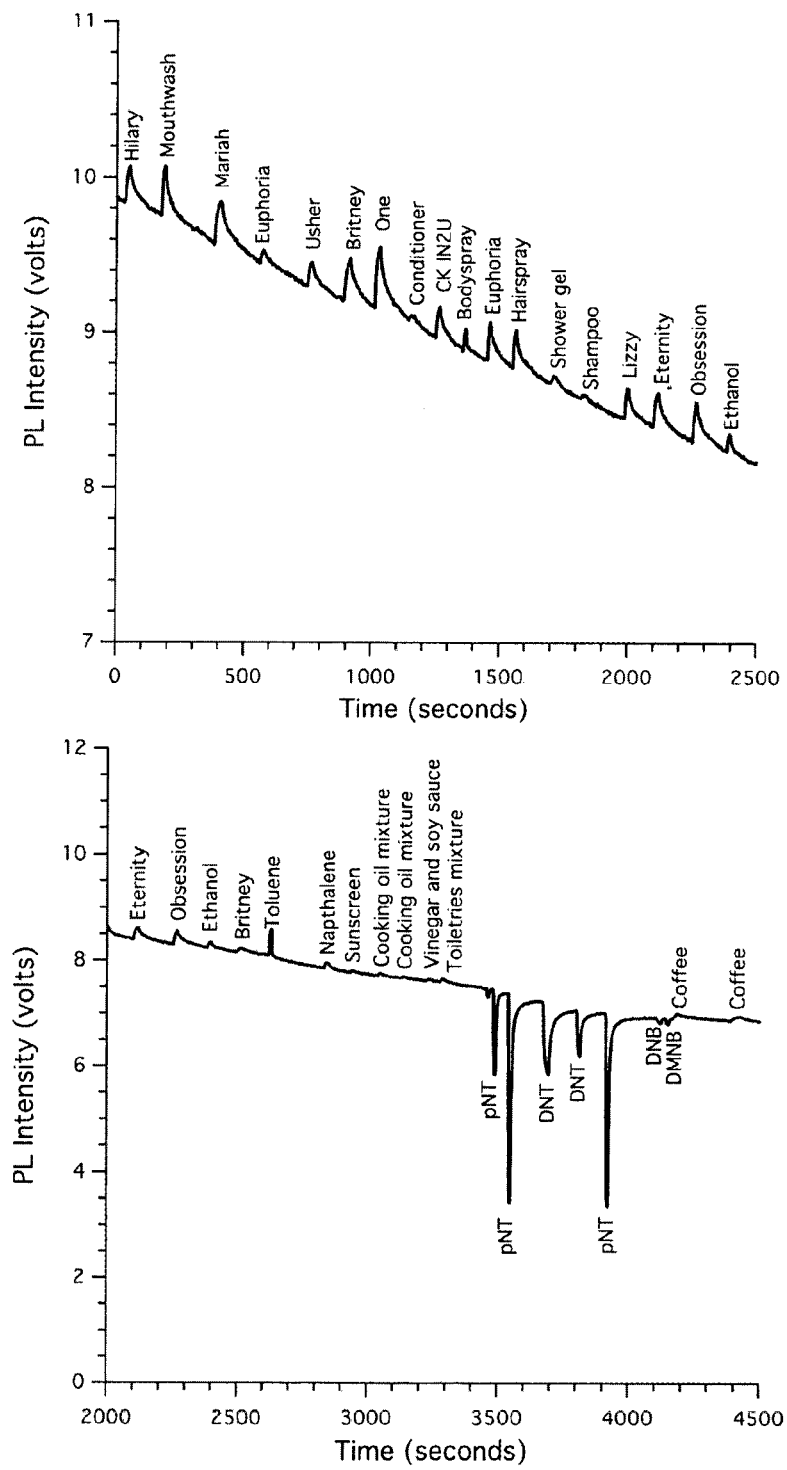
Figure 10B:
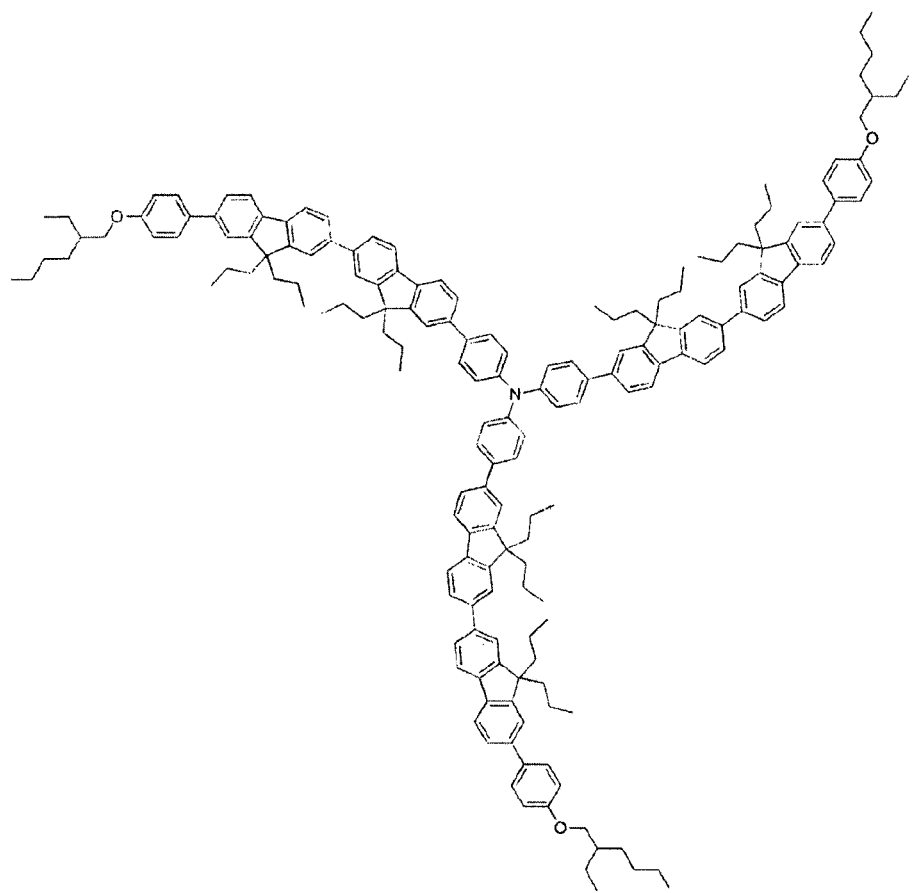
Figure 11:
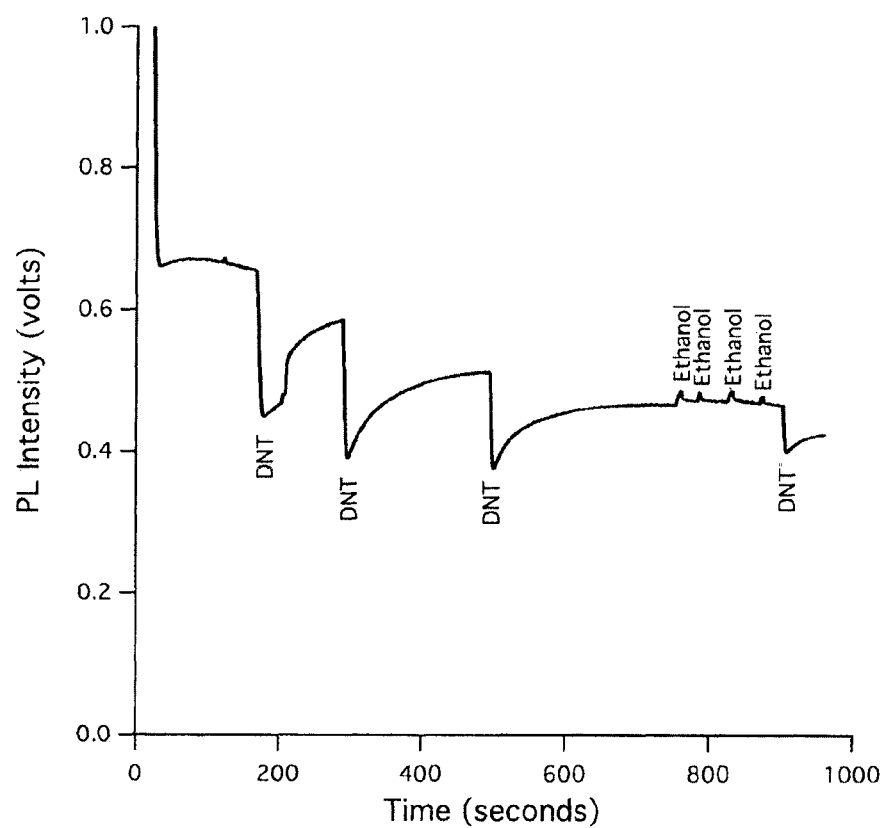
Figure 11:
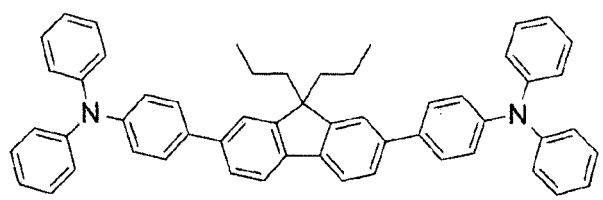
Figure 12:
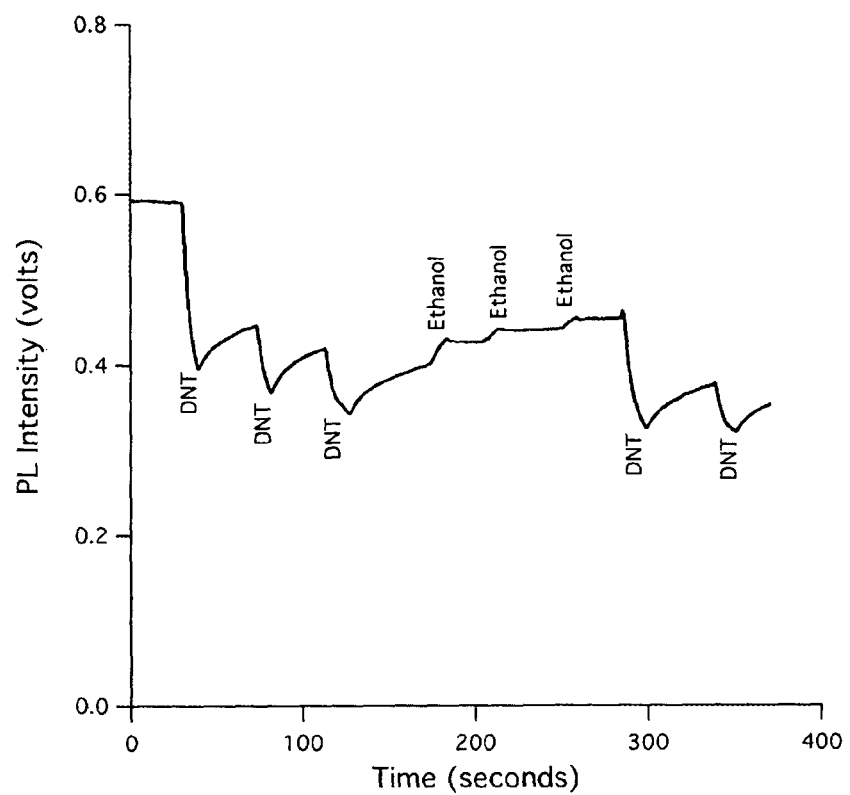
Figure 12:
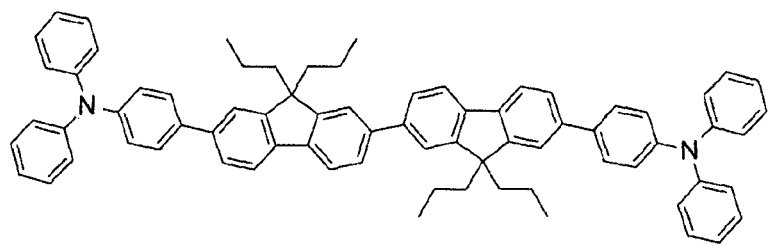
Figure 13:
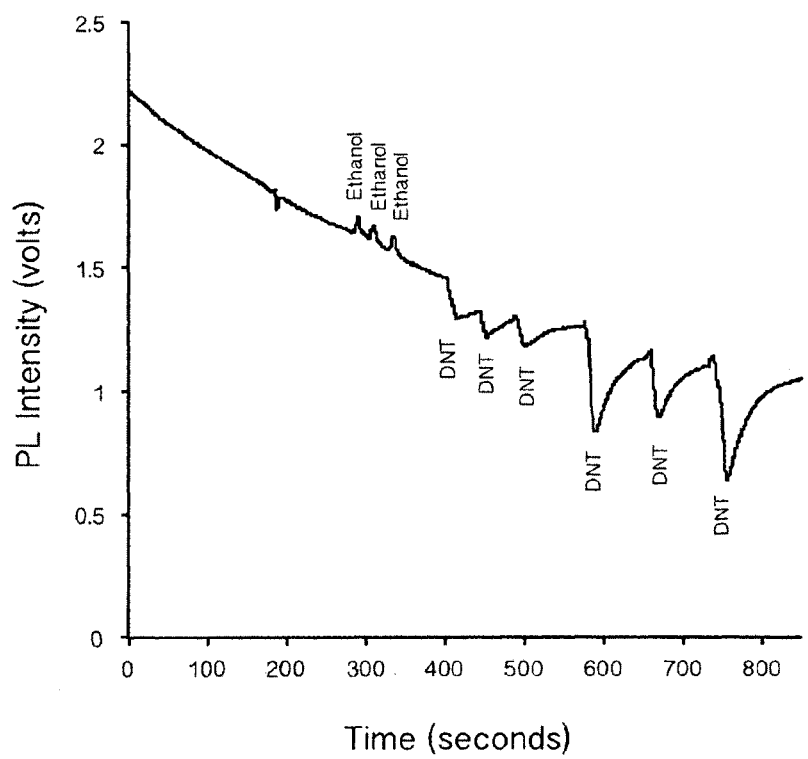
Figure 13:
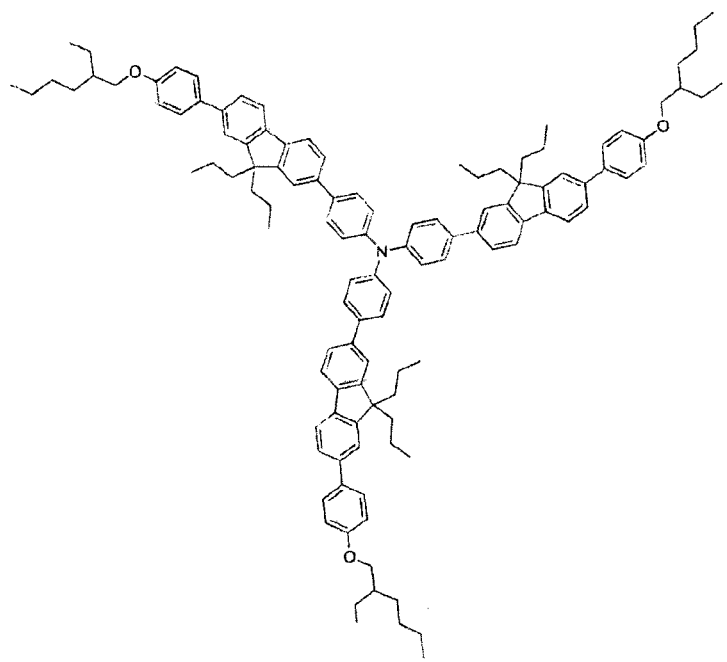

FIG. 10*a* is a plot of photoluminescence intensity versus time when a sensing device including the triaryl amine compound shown in FIG. 10*b* is exposed to a variety of analytes;

FIG. 11 is a plot of photoluminescence intensity versus time when a sensing device including the triaryl amine compound shown is exposed to a variety of analytes;

FIG. 12 is a plot of photoluminescence intensity versus time when a sensing device including the triaryl amine compound shown is exposed to a variety of analytes; and FIG. 13 is a plot of photoluminescence intensity versus time when a sensing device including the triaryl amine compound shown is exposed to different of analytes.

DETAILED DISCUSSION OF THE INVENTION

In accordance with the present invention it has been found that certain compounds comprising a triaryl amine moiety exhibit a characteristic luminescence response when exposed to analyte molecules of particular interest, i.e. explosives and explosives-related materials. The nature of this response means that these compounds have great potential in the kind of direct sensing methodology described. The underlying mechanism associated with that methodology is of course known, but the present invention is believed to represent a significant advance in the art.

In broad terms, the method of the invention comprises:
(i) allowing a luminescent compound comprising a triaryl amine moiety to interact with the analyte and measuring the luminescent properties of the compound during exposure to the analyte;
(ii) detecting a difference between the luminescent properties measured in step (i) and the luminescent properties of the compound prior to measurement of luminescent properties in step (i); and
(iii) determining whether the analyte is present based on the difference in luminescent properties detected in step (ii).

In the context of the method of the invention it is possible for step (ii) to be undertaken in a variety of ways. In one embodiment, this step may be undertaken based on actual measurement of the luminescent properties of the compound comprising a triaryl amine moiety prior to measurement of luminescent properties in step (i). In this embodiment the invention provides a method of detecting an analyte, which method comprises:

(a) exciting a luminescent compound comprising a triaryl amine moiety and measuring the luminescent properties of the compound;
(b) allowing the compound to interact with the analyte and measuring the luminescent properties of the compound due to exposure to the analyte;
(c) detecting a difference between the luminescent properties measured in steps (a) and (b); and
(d) determining whether the analyte is present based on the difference in luminescent properties detected in step (c).

This embodiment relies on there being a change in measured luminescent properties as a result of exposure of the luminescent compound to an analyte. The real time implementation of this embodiment would involve excitation and measurement of luminescent properties prior to sampling for an analyte. Determining the initial luminescent response of the compound (i.e. before exposure to an analyte) is important in order to give a control or base reading against which any subsequent change in luminescent response can be assessed.

In certain embodiments triaryl amine compounds used in the present invention may show advantageous selectivity towards a variety of analytes. Specifically, the compounds can show luminescence quenching in the presence of explosive analytes and/or taggants. More specifically, the compounds show luminescence quenching in the presence of analytes and/or taggants that contain one or more nitro groups. Preferably, the compounds show luminescence quenching in the presence of a nitroaromatic analyte.

Broadly speaking, the invention is believed to be of value since it provides a viable alternative to existing technology. However, of particular significance is the fact that that triaryl amine compounds used in accordance with the invention exhibit a fundamentally different photoluminescent response to certain analytes when compared with compounds, such as conjugated polymers, used in existing sensors that operate on the same principles. More particularly, triaryl amine compounds used in the present invention may exhibit a characteristic luminescence response to analytes that allows explosives and explosives-related materials to be readily detected as against every-day chemicals that would otherwise have an impact on detection. In other words, triaryl amine compounds used in accordance with the invention may provide qualitative detection selectivity with respect to explosives and explosives-related materials. More specifically the triaryl amine compounds may exhibit a detectable response (decrease or increase) in the luminescence in the presence of the explosives and explosives-related materials whereas there is no response, or no significant response, in the photoluminescence in the presence of non-explosive related (everyday) materials such as perfumes, coffee etc. In an alternative embodiment the triaryl amine compounds may exhibit a particular response (e.g. a decrease) in the luminescence in the presence of the explosives and explosives-related materials whereas the opposite response (an increase in the context of the example given) in the photoluminescence in the presence of non-explosive related (everyday) materials. These response characteristics are advantageous when it comes to detecting analytes of interest.

Whilst the triaryl amine compounds used in accordance with the present invention may be useful for selective detection of a variety of target analytes (and the scope of this may be investigated for any given compound), the compounds are believed to have particular value in relation to the selective detection of explosives and explosives-related materials as analytes. In the context of the present invention these analytes are nitrogen-containing species and include explosives per se as well as related (functional) materials such as accelerants, taggants and the like.

By way of specific example, the analyte may be selected from 2,4,6-trinitrotoluene (TNT high explosive), 2,3-dinitro-2,3-dimethylbutane (a tagiant typically used in the explosive Semtex), 2,4,6-trinitro-m-xylene (TNX), 2,4,6-trinitrochlorobenzene (picryl chloride), 2,4,6-trinitrophenol (picric acid); ammonium picrate (Explosive D); 2,4,6-trinitro-m-cresol (TNC), 2,4,6-trinitroresorcinol (styphnic acid), 2,4,6-trinitroanisole (TNA, methyl picrate), 2,4,6-trinitrophenetole (TNP, ethyl picrate), 2,4,6-trinitroaniline (picramide, 1-monoamino-2,4,6-trinitrobenzene, MATB), 1,3-diamino-2,4,6-trinitrobenzene (DATB), 1,3,5-triamino-2,4,6-trinitrobenzene (TATB), and 2,4,6-N-tetranitro-N-methylaniline (tetryl, 2,4,6-trinitrophenylmethyinitramine), 2-amino-4,6-dinitrotoluene, 4-amino-2,6-dinitrotoluene, 2-amino-4-nitrotoluene, 3,5-dinitroaniline, 1,3-dinitrobenzene, 1,4-dinitrobenzene, 1,2-dinitrobenzene, 2,4-dinitrotoluene, 2,3-dinitrotoluene, 2,6-dinitrotoluene, nitromethane, 3-nitroaniline, 2,4,6-trinitroaniline, nitroamines such as 1,3,5-trinitroperhydro-1,3,5-triazine, and nitroesters such as [3-nitrooxy-2,2-bis(nitrooxymethyl)propyl]nitrate. It will be appreciated that these and other nitrated analytes may be found with other compounds in an explosive mixture. It will also be appreciated that analytes need to have sufficient vapour pressure to be detectable.

The present invention relies on the use of certain compounds that have characteristic structural features and optical properties. With respect to structure the compounds can broadly be classified as luminescent triaryl amines and the presence of the triaryl amine moiety is believed to be significant to the usefulness of the compounds in the context of the present invention.

The triaryl amine compound must also exhibit suitable optical properties to be useful in the present invention. That is, the compounds must be capable of interacting with an analyte molecule thereby causing a detectable change in luminescence intensity. Preferably, the compounds are fluorescent.

Furthermore, triaryl amine compounds useful in the present invention will generally be used in sensor devices in the solid phase, usually as coatings/films on a substrate. It is obviously important that the compounds retain the desirable optical properties when provided in this form. Sensor devices useful in the context of the present invention will be discussed in more detail below.

Characterising the structure of the compounds in more detail, they can be regarded as conjugated compounds that comprise a triaryl amine moiety. Generally, one or more, preferably one, conjugated molecular structure is bound to each of the three aryl groups of the triaryl amine moiety. The conjugated molecular structure is bonded to the aryl group in such a way so as to preserve conjugation with the aryl group. The conjugated molecular structures may be the same or different.

In this context the term "conjugated molecular structure" means a structure comprising at least 5 carbon atoms with alternating single and multiple bonds that provide delocalization of electrons. The conjugated molecular structure may include alkenyl, alkynyl and/or conjugated cyclic moieties. The presence of conjugated molecular structures attached to the triaryl amine compounds used in the present invention is critical to their usefulness in the context of the present invention. This may be understood with reference to the underlying mechanism by which the compounds are believed to function in the present invention. Absorption by the compound of a photon produces a singlet excited state. An analyte molecule may interact with the excited triaryl amine compound leading to oxidation of the excited state with the result that there is no luminescence. This effect is known as oxidative luminescence quenching. The conjugated molecular structure may be at least partially conjugated provided that the intended functionality in the context of the invention is preserved.

Advantageously, triaryl amine compounds useful in the present invention have been found to exhibit selective luminescence quenching when exposed to explosives and explosives-related materials. In contrast, the compounds may exhibit a qualitatively different fluorescent response in the presence of everyday chemicals. It will be appreciated that for oxidative luminescence quenching to occur the analyte must have an electron affinity sufficient to separate the exciton that is formed on excitation of the triaryl amine compound. It is well known in the art how to modulate the optical and electronic properties of conjugated molecules and this can be applied to the optical and electronic properties of the triaryl amine compounds used in the current invention.

The conjugated molecular structure may be polymeric in character in the sense that it includes repeat units within its structure. However, this is not essential and the conjugated molecular structure may be non-polymeric in character. In the latter case, the conjugated molecular structure may include linear and/or branched moieties. When branched, the conjugated molecular structure may be a dendritic structure. In the case of a dendrimer the triaryl amine moiety could be at the centre of the dendrimer, in the dendron or both.

It will be appreciated that by its very structure the triaryl amine moiety provides branching in the structure of the overall compound. The triaryl amine moiety may be the only part of the molecule that provides branching or it may provide one of several branching points depending upon the architecture of the conjugated molecular structure. From this it will be understood that when the triaryl amine compound is a polymer, the triaryl amine moiety could be part of the main chain, part of a side chain group, or both. It will also be appreciated that there could be more than one triaryl amine group in a material. For example, in a polymer the triaryl amine group could be present as part of a 'monomer unit' repeated along the polymer backbone. Also each DENDRON of a dendrimer could contain one or more triaryl amine groups. In the case where more than one triaryl amine group is present and they are linked sequentially an individual aryl group may be attached to two or more nitrogen atoms.

The conjugated molecular structure may comprise one or more aryl or heteroaryl groups that can be linked directly together or via one or more alkenyl or acetylenyl groups. The connection of the conjugated molecular structure to the aryl moieties of the triaryl amine group can be via an aryl, heteroaryl, alkenyl or acetylenyl carbon atom of the conjugated molecular structure. Typically, however, connection is via an aryl or heteroaryl moiety of the conjugated molecular structure. Where connection is via a heteroaryl group, this may be via a heteroatom. In heteroaryl groups the heteroatom may be N, O or S. The aryl groups are usually benzene rings, and these are typically substituted at position 2, 3, 4, 5 or 6 to provide the remainder of the conjugated molecular structure. The heteroaryl group is usually a 5- or 6-membered ring structure, and may be selected from thiophene, pyridine, pyrimidine, triazine, etc. The use of poly-aromatic ring structures is also possible. The use of fused ring aryl and heteroaryl ring systems is also possible, including naphthalene, anthracene, carbazole, fluorene etc. It is also possible that two or more aryl groups of the triaryl amine compound are linked by a conjugated molecular structure. A fundamental requirement however is that the number and combination of conjugated molecular structures present in the triaryl amine compound must be such that the singlet excited state of the compound can be oxidised by the analyte. It will be further appreciated that the aryl and/or heteroaryl groups can be substituted with further non-conjugated groups to provide the required solubility and processability. A non-exhaustive list of suitable non-conjugated (surface) groups is included below.

In terms of a molecular formula the conjugated molecular structure may be represented by the formula (I):

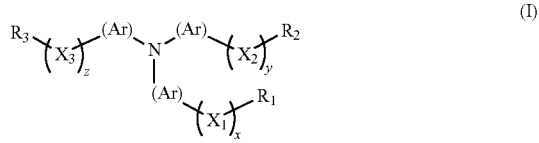

in which each Ar represents an aryl moiety, $R_1$, $R_2$, $R_3$ are the same or different conjugated molecular structure comprised of moieties as defined above, $X_1$, $X_2$, $X_3$ are independently selected from conjugated moieties and/or nitrogen atoms linking Ar with respective groups $R_1$, $R_2$, $R_3$ and x, y, and z are independently 0, 1, 2, 3, or 4.

When x, y or z is greater than 1, the respective groups $X_1$, $X_2$ and $X_3$ may be the same or different. For example, when x is 2, the linkage between the group Ar and the group $R_1$ will be of formula —$X_1$—$X_1$— in which each $X_1$ may be the same or different.

When one or more of $X_1$, $X_2$ and $X_3$ is a nitrogen atom, the nitrogen atom is bonded directly to a conjugated group or moiety so that the lone pair of the nitrogen atom can interact with the conjugated group or moiety. Typically, when one or more of $X_1$, $X_2$ and $X_3$ is a nitrogen atom this nitrogen atom is usually part of a triaryl amine substituted moiety.

In an embodiment the aryl group may be selected from phenyl, napthyl, anthracenyl, acenapthyl, fluorenyl and azulenyl. In an embodiment each Ar group is the same and is phenyl. In another embodiment, each group Ar is phenyl and $R_1$, $R_2$, $R_3$ are the same.

Typically, $X_1$, $X_2$, $X_3$ are independently selected from aryl, heteroaryl, alkenyl or acetylenyl groups.

It is also possible that one or more of $X_1$, $X_2$ and $X_3$ is a conjugated repeat unit of a polymer chain or a conjugated dendrimer.

In an embodiment, when x and y are zero, $R_1$ and $R_2$ may constitute the main part of a polymer chain together with two of the aryl groups and the nitrogen atom of the triaryl amine moiety of the molecule, with the remaining aryl group, $X_3$ if present and $R_3$ providing chain-branching. Alternatively, one of the groups, say $R_1$, may be a polymer chain with the remainder of the molecule being present as a pendant group (side chain) of the polymer chain. In this case the group $R_1$ will also need to provide a point of attachment to the polymer backbone. The remaining groups, $R_2$ and $R_3$ may be conjugated molecular structures as defined above, for example dendrons or simple linear-conjugated species.

Of course, the structure represented by formula (I) may be part of a branched compound such as a dendrimer. In that case at least one of $R_1$, $R_2$, and $R_3$ has to be a dendron. Alternatively, $R_1$, $R_2$, and $R_3$ can simply be linear conjugate sequences, i.e. the N atom is at the centre.

When at least one conjugated molecular structure is a dendron, the compound may be represented by formula I in which one or more of $R_1$, $R_2$, and $R_3$ may be the same or different group of formula:

-(DENDRON)-B in which DENDRON represents a conjugated dendritic molecular structure comprising a plurality of chain branches each of which terminates with a distal aryl or heteroaryl group, and B represents an optional surface group attached to the distal aryl and/or heteroaryl group terminating a chain branch. The individual chain branches of DENDRON may be the same or different. When present the surface groups in DENDRON may be the same or different. When a surface group is not present on a particular chain branch, that chain branch will terminate with the terminal aryl or heteroaryl group.

In this embodiment the outer surface presented by the molecule provides an element of control of the solubility and processability of the molecule and thus changes to the internal electronic structure should be possible without unacceptably affecting the processing properties and vice versa. Therefore, this embodiment may provide an opportunity of optimizing the electronic and processing properties independently which should give improved manufacturability of electronically optimized materials.

The surface groups may include halogen, $C_{1-10}$ alkyl, $C_{2-10}$ alkenyl, —C(O)R wherein R is hydrogen or $C_{1-10}$ alkyl, —$CO_2R$ wherein R is hydrogen or $C_{1-10}$ alkyl, hydroxy, $C_{1-10}$ alkoxy, $C_{2-10}$ alkenyloxy, $C_{1-10}$ alkylthio, $C_{2-10}$ alkenylthio, $C_{1-10}$ haloalkyl, $C_{2-10}$ haloalkenyl, $C_{1-10}$ haloalkoxy, $C_{2-10}$ haloalkenyloxy, amino, $C_{1-10}$ alkylamino, di($C_{1-10}$)alkylamino, $C_{6-14}$ aryloxy, —$O_2SR$ or —$SiR_3$ wherein each R is the same or different and represents hydrogen, $C_{1-10}$ alkyl or $C_{2-10}$ alkenyl. Other suitable substituents include hydroxy($C_{1-10}$)alkyl and hydroxyhalo($C_{1-10}$)alkyl groups, for example hydroxy($C_{1-4}$)alkyl and hydroxyhalo($C_{1-4}$)alkyl groups. A surface group that allows further reaction may interact to provide cross-linking. In this case the surface group may be selected from, for example, as alkene, (meth)acrylate, an oxetane containing group or silicon-containing group.

More particularly, DENDRON may be the same or different group of the formula:

-[A-(ARM)$_d$]-B in which A is a first aryl or heteroaryl moiety of the DENDRON, ARM represents a group of one or more of alkenyl, alkynyl, aryl or heteroaryl moieties for a first generation dendrimer or for higher generation dendrimers a dendritic arm extending from A, d is equal or greater than 2, and B is as defined before.

In another embodiment the compounds of formula (I) may be represented by formula (Ia):

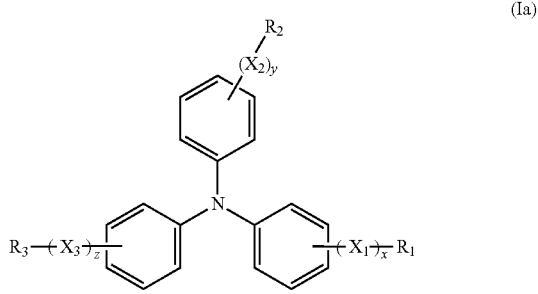

in which x, y, z, $X_1$, $X_2$, $X_3$, $R_1$, $R_2$ and $R_3$ are as defined above.

In an embodiment each of $X_1$, $X_2$, $X_3$, $R_1$, $R_2$, and $R_3$ occupy the ortho-, meta- or para-position on the phenylene ring. Preferably, each of $X_1$, $X_2$, $X_3$, $R_1$, $R_2$, and/or $R_3$ are in the para-position relative to the nitrogen atom. Accordingly, in a further aspect the compounds of formula (I) may be represented by formula (Ib):

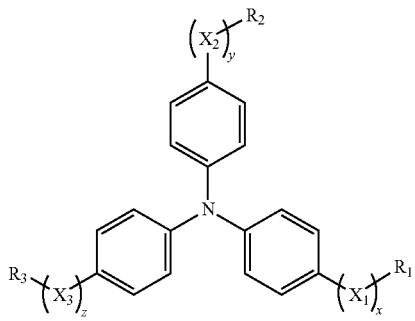

in which x, y, z, $X_1$, $X_2$, $X_3$, $R_1$, $R_2$, and $R_3$ are as defined above.

In an embodiment $X_1$, $X_2$ and $X_3$ are a substituted thiophenyl group, preferably a substituted 2,5-thiophenyl group of formula:

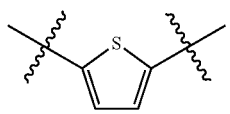 [SMILES: *c1ccc(*)s1]

Accordingly, in a further embodiment the compound of formula (I) may be represented by formula (Ic):

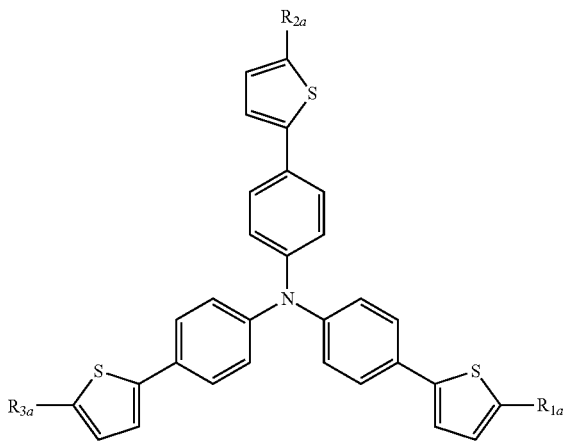

in which $R_{1a}$, $R_{2a}$ and $R_{3a}$ represent the remainder of the conjugated molecular structure represented by $R_1$, $R_2$ and $R_3$. In an embodiment $R_{1a}$, $R_{2a}$ and $R_{3a}$ are bonded to the thiophenyl group by the same type of substituted aryl or substituted phenyl moiety.

Accordingly, in a further embodiment the compound of formula (I) may be represented by formula (Id):

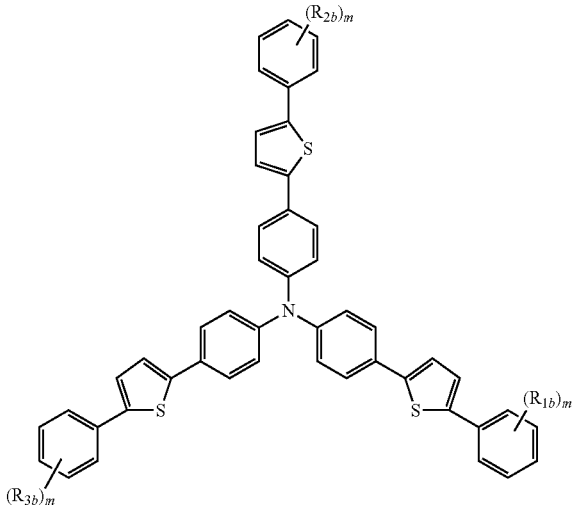

In an embodiment $R_{1b}$, $R_{2b}$ and $R_{3b}$ are independently selected from $C_1$-$C_{20}$ alkyl, or $C_1$-$C_{20}$alkoxy when m is 1, and when m is 2 or more an optionally substituted ARM as defined above.

In an embodiment when m is 1, each $R_{1b}$, $R_{2b}$ and $R_{3b}$ preferably occupies the para position of the phenyl ring. In this case $R_{1b}$, $R_{2b}$ and $R_{3b}$ are the same or different, preferably the same, $C_1$-$C_{20}$alkoxy, such as $C_2$-$C_{15}$alkoxy or $C_3$-$C_{10}$alkoxy.

In an embodiment when m is 2, each $R_{1b}$, $R_{2b}$ and $R_{3b}$ is the same or different, preferably the same, ARM is an optionally substituted phenyl moiety. When the phenyl moiety is substituted the substituent B may be selected from $C_1$-$C_{10}$ alkyl and $C_1$-$C_{10}$alkoxy. Preferably, the phenyl moiety attached to the thiophene ring is substituted at the meta-positions by the ARM groups.

In another embodiment when m is 2, each ARM has a group B located at the para position and is selected from $C_1$-$C_{10}$ alkyl or $C_1$-$C_{10}$alkoxy.

In an embodiment and in respect of compounds of formula (Ia) and (Ib), $R_1$, $R_2$ and $R_3$ are each bonded to the phenyl moiety by the same or different, preferably the same, substituted aryl group selected from substituted phenyl, substituted napthyl, substituted anthracenyl, substituted acenapthyl, substituted fluorenyl, or substituted azulenyl, preferably substituted fluorenyl.

In this case the compounds of formula (I) may be represented by formula (Ie)

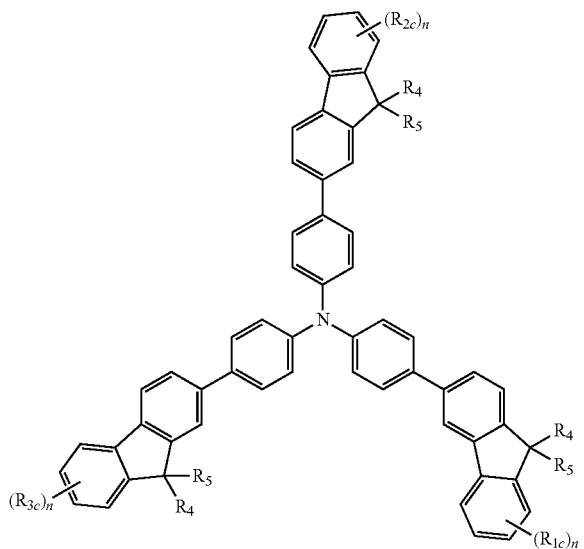 (Ie)

in which $R_{1c}$, $R_{2c}$ and $R_{3c}$ represent the remainder of the conjugated molecular structure represented by $R_1$, $R_2$ and $R_3$. For example, $R_{1c}$, $R_{2c}$ and $R_{3c}$ may be independently selected from optionally substituted aryl, or optionally substituted heteroaryl, n at each occurrence is independently 1, 2, or 3; and $R_4$ and $R_5$ at each occurrence is independently $C_1$-$C_{10}$ alkyl, $C_1$-$C_{10}$alkoxy, glycols of differing lengths, crosslinkable groups such as vinyl, methacrylate or oxetanes that can be attached via a flexible chain.

In an embodiment the compounds of formula (I) or (Ie) are represented by compounds of formula (If):

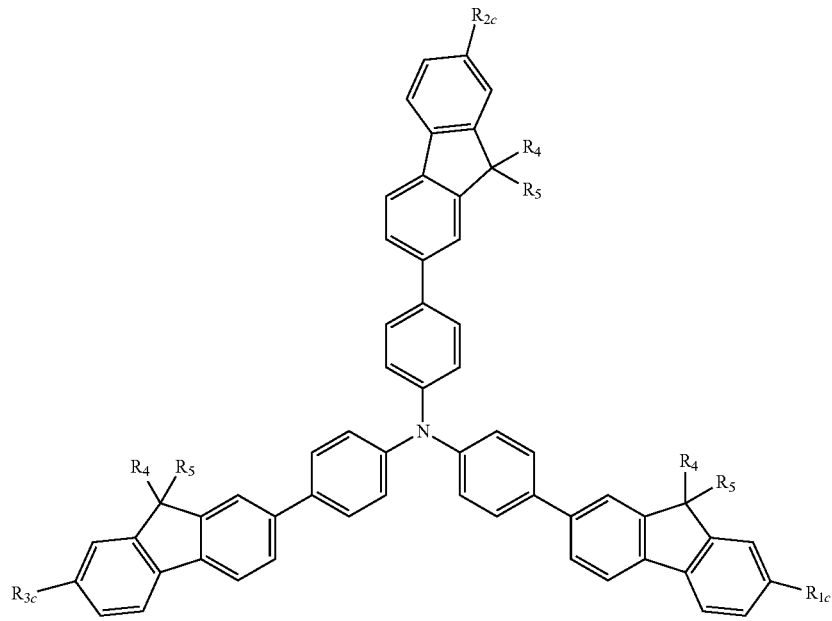 (If)

in which $R_{1c}$, $R_{2c}$ and $R_{3c}$, $R_4$, and $R_5$ are as defined above for formula (Ie).

In an embodiment and with reference to formulae (Ic) and (If), $R_{1c}$, $R_{2c}$ and $R_{3c}$ are the same and represent optionally substituted phenyl or optionally substituted fluorenyl.

In another embodiment the compounds of formula (I), (Ie) or (If) may be represented by compounds of formula (Ig):

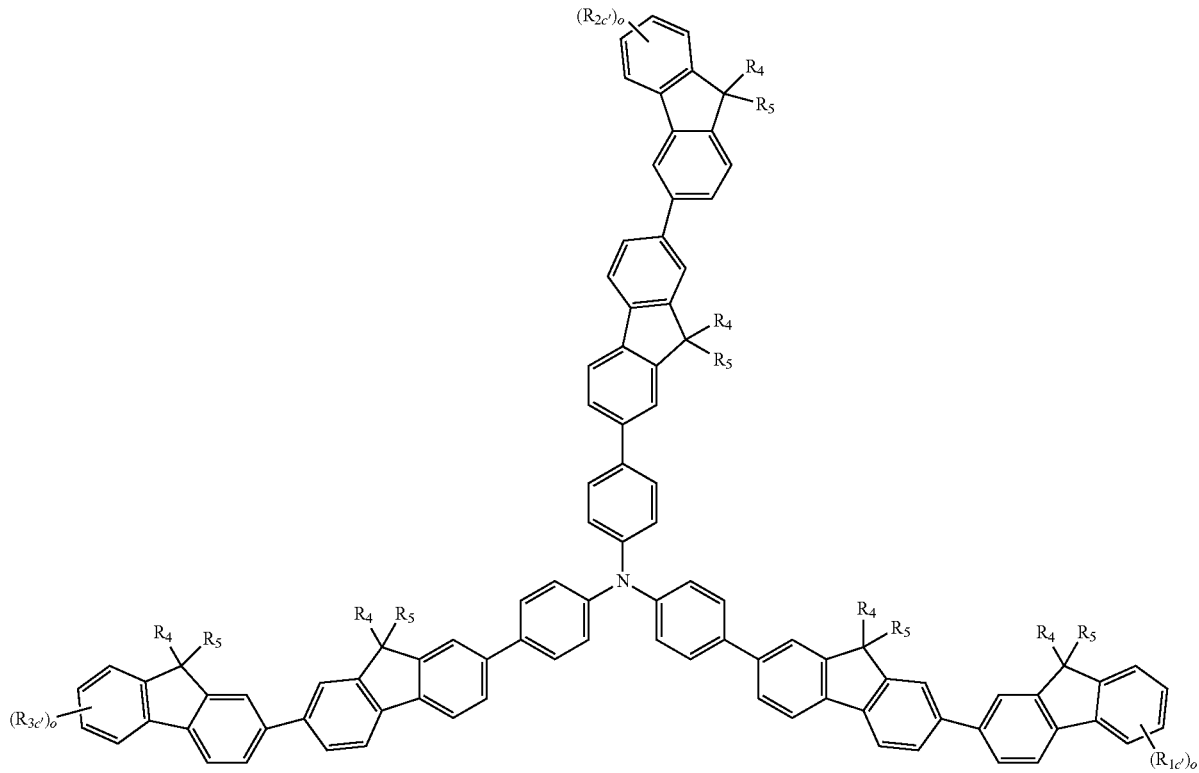

(Ig)

in which $R_{1c'}$, $R_{2c'}$ and $R_{3c'}$ represent the remainder of the conjugated molecular structure represented by $R_1$, $R_2$ and $R_3$. For example, $R_{1c'}$, $R_{2c'}$ and $R_{3c'}$ may be independently selected from optionally substituted aryl or optionally substituted heteroaryl; o at each occurrence is independently 1, 2, or 3; and $R_4$ and $R_5$ at each occurrence is independently $C_1$-$C_{10}$ alkyl, $C_1$-$C_{10}$ alkoxy, glycols of differing lengths, crosslinkable groups such as vinyl, methacrylate or oxetanes that can be attached via a flexible chain. In an embodiment $R_{1c'}$, $R_{2c'}$ and $R_{3c'}$ are the same and represent substituted phenyl. In a further embodiment $R_{1c'}$, $R_{2c'}$ and $R_{3c'}$ are the same and represent phenyl substituted 1 or 2 times with $C_1$-$C_{20}$ alkyl or $C_1$-$C_{20}$ alkoxy.

Herein reference is made to certain groups being optionally substituted. Examples of possible substituent groups include halogen, $C_{1-10}$ alkyl, $C_{2-10}$ alkenyl, —C(O)R wherein R is hydrogen or $C_{1-10}$ alkyl, —$CO_2$R wherein R is hydrogen or $C_{1-10}$ alkyl, hydroxy, $C_{1-10}$ alkoxy, $C_{2-10}$ alkenyloxy, $C_{1-10}$ alkylthio, $C_{2-10}$ alkenylthio, $C_{1-10}$ haloalkyl, $C_{2-10}$ haloalkenyl, $C_{1-10}$ haloalkoxy, $C_{2-10}$ haloalkenyloxy, amino, $C_{1-10}$ alkylamino, di($C_{1-10}$)alkylamino, $C_{6-14}$ aryloxy, —$O_2$SR or —$SiR_3$ wherein each R is the same or different and represents hydrogen, $C_{1-10}$ alkyl or $C_{2-10}$ alkenyl, $C_{6-14}$ arylthio, $C_{6-14}$ aryl and 5- to 10-membered heteroaryl, and wherein the substituents are themselves unsubstituted or substituted, or fluoro. Other suitable substituents include hydroxy($C_{1-10}$)alkyl and hydroxyhalo ($C_{1-10}$)alkyl groups, for example hydroxy($C_{1-4}$)alkyl and hydroxyhalo($C_{1-4}$)alkyl groups.

Specific examples of triaryl amine compounds useful in the present invention include the following:

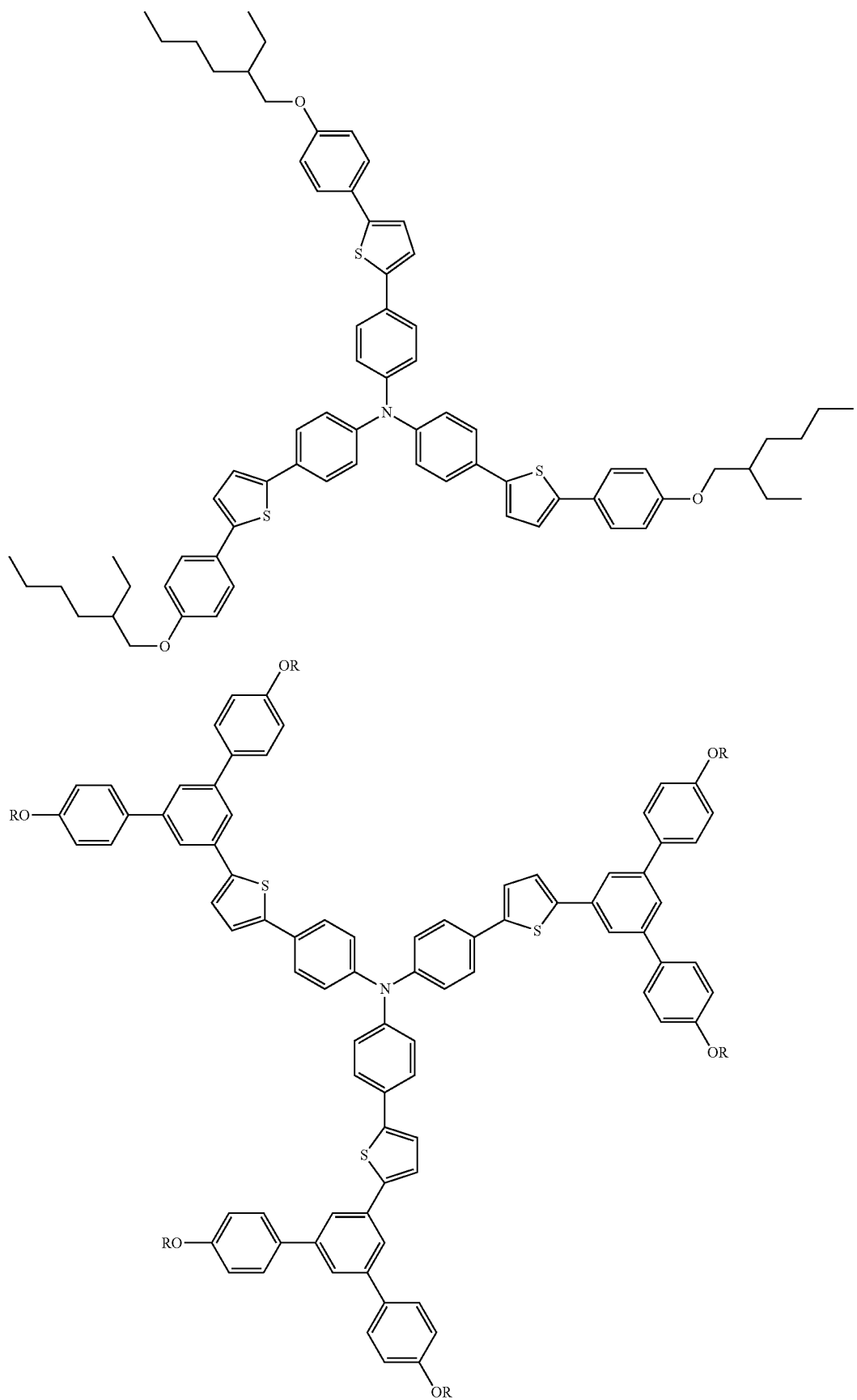

-continued
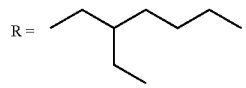
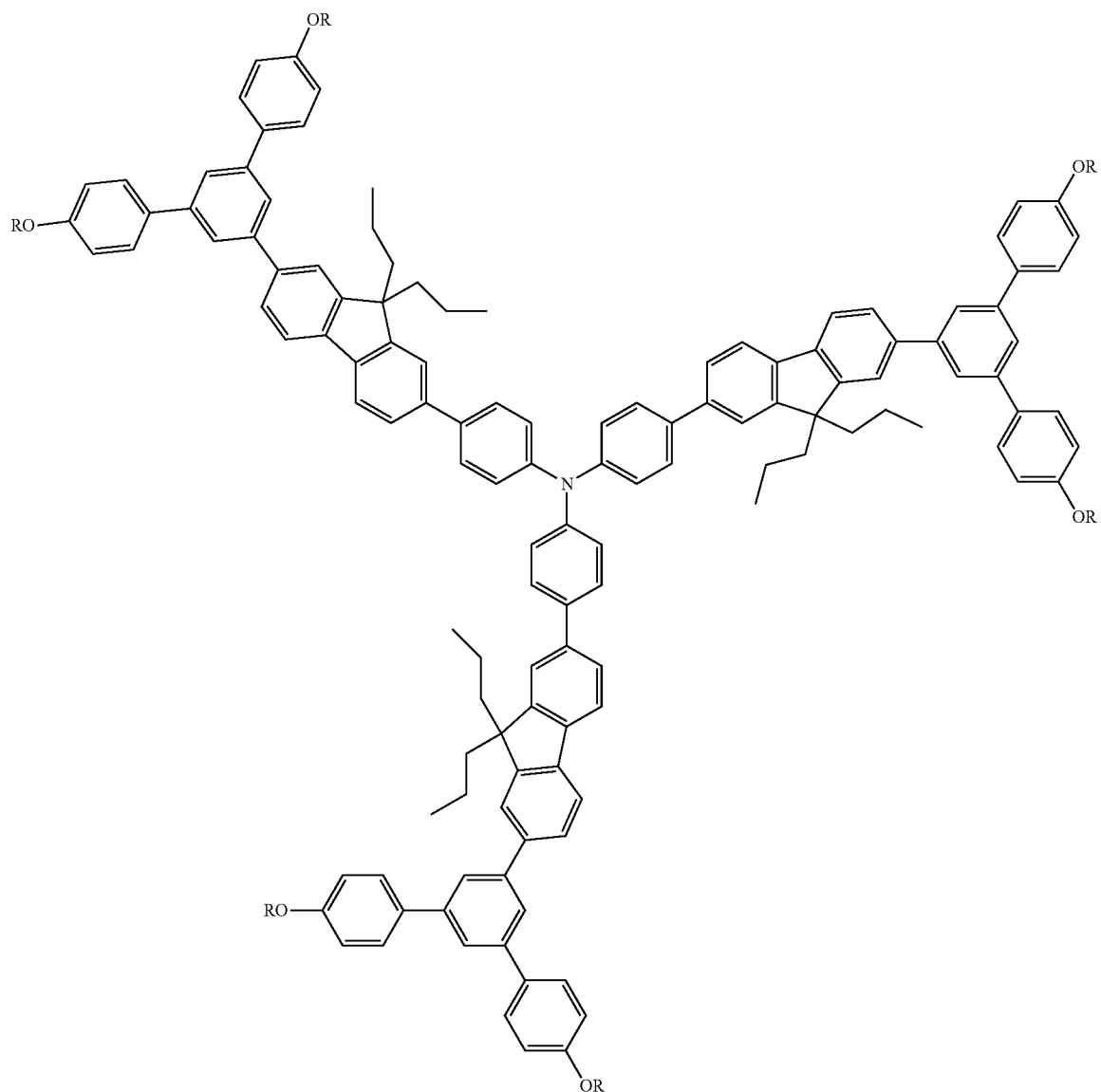
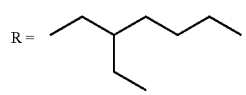

-continued

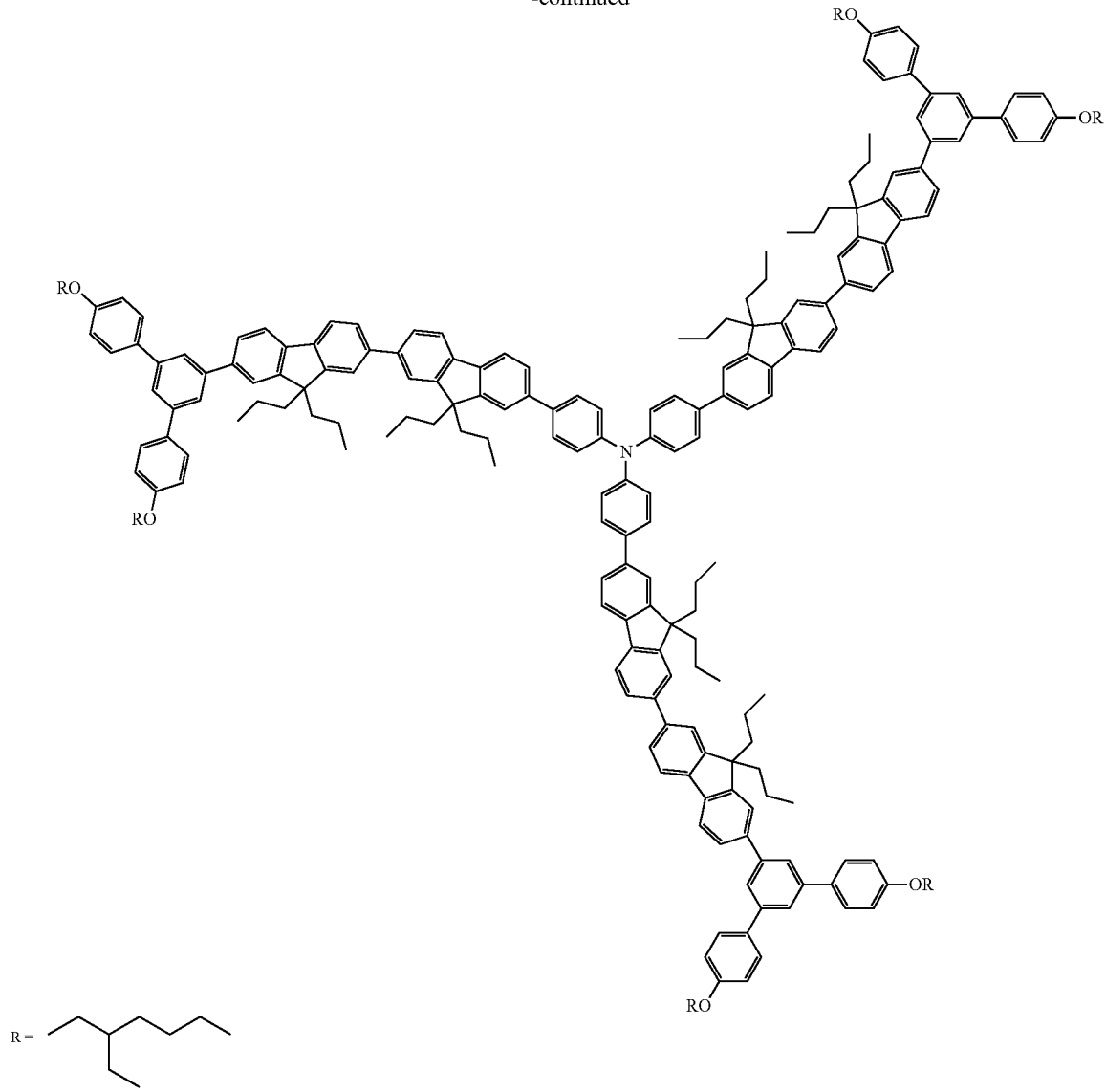

Triaryl amine compounds used in the present invention may be made by the application or adaptation of known techniques. By way of example, reference may be made to WO01/59030, Ellen J. Wren, Karyn Mutkins, Muhsen Aljada, Paul L. Burn,* Paul Meredith* and George Vamvounis Polym. Chem., 2010, 1, 1117-1126.

Figure 1:
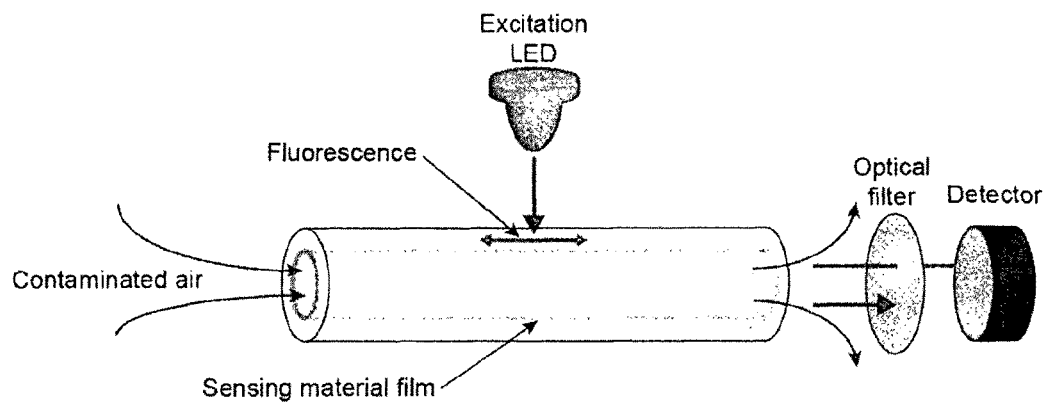
FIG. 1 is a schematic showing components of a sensing device.

The sensor devices in which the triaryl amine compounds described herein may be used are of conventional design and are operated in conventional manner. A typical device is shown in FIG. 1. An excitation source is used to supply the electromagnetic radiation that interacts with the compound being used to cause the compound to generate light. The compound is provided on a suitable substrate, thereby forming a sensing element. The excitation source may be an LED, a laser, cathode lamp, or the like. The device also includes a light detector that receives light from the compound. This detector delivers an output signal that is indicative of the intensity of light emitted by the compound. The device will also include componentry (microprocessors) that allows the output of the light detector to be visualized or otherwise represented for interpretation. The device will also include one or more temperature control elements for regulating and detecting the temperature of parts of the device as necessary for optimum operation.

In the context of the present invention, the triaryl amine compound will be provided as a coating/film on a substrate over or through which a gas to be analysed is passed or delivered. Herein the expression "sensing element" is used to denote the coated substrate. Interestingly, the form the substrate takes has been found to influence the efficacy of triaryl amine compounds in selectively detecting analyte molecules of interest (explosives and explosives-related materials). Thus, it has been found that non-planar substrates may be preferred. Depending upon geometry the substrate material may need to be effectively transparent to the wavelength of light that is to be used to excite the triaryl amine compound used. The substrate material must also be non-reactive with respect to target analytes.

It has also been found that the thickness of the coating/film of triaryl amine compound has an impact on detection efficacy. The thickness may be optimized by experimentation for a given combination of substrate and triaryl amine compound. Typically, the coating/film thickness will be up to 100 nm, for example in the range 10-100 nm. The compound may be deposited by conventional techniques.

In one embodiment the substrate may take the form of a tube with the compound provided on the internal surface of the tube. The tube typically has a circular cross-section. The optimum dimensions for the tube, as well as suitable materials from which the tube is made, may be determined experimentally. In a preferred embodiment the compound is provided on the internal surface of a capillary tube. The capillary tube may be made of a glass, such as a borosilicate glass, or silica. Typically, the capillary will have an internal diameter of from 10 μm to 1 mm. The length of the capillary is usually no longer than 100 mm. Useful capillaries with the required externally and internal diameters are commercially available and can be cut to the appropriate length. For example, such tubes can have the following dimensions: length=30 or 54 mm with the outside diameter of 5 mm and internal diameter of 0.5 mm.

FIG. 1 shows a simplified arrangement of components that would be used in a sensor device. The figure shows a capillary tube coated on its inner surface with a thin film of optically active triaryl amine compound. The compound is excited by exposure to light of a suitable wavelength and the compound's response to this in terms of photoluminescence measured using a suitable detector. The excited compound is then exposed to air to be analysed (termed "contaminated air" in the figure). Any change in luminescence intensity due to analyte(s) present in the air interacting with the excited compound is also detected. The response of the excited compound to a range of analytes has been pre-determined and this enables the result obtained to be interpreted. However, the qualitative response per se of triaryl amine compounds used in the present invention may allow immediate identification of explosives and explosives-related materials, even when present with everyday chemicals, such as cosmetics and perfumes.

The substrate bearing the triaryl amine compound (i.e., the sensing element) will be replaced from time to time and as such can be regarded as a consumable. The sensing capability of the device may also be tailored/tuned by installing a substrate bearing a triaryl amine compound having the desired sensing capability with respect to the analyte of interest. Other changes may then also need to be made based on the compound being used, e.g. device operating temperature, excitation wavelength etc. It will be appreciated from this that the sensing element is a commercial commodity in its own right for use with a sensing device that is adapted to receive the substrate. The sensing element also forms part of the present invention.

The present invention also provides a sensing device including a sensing element as described herein.

Embodiments of the present invention are illustrated with reference to the following non-limiting examples and comparative examples.

Comparative Example 1

Figure 2:
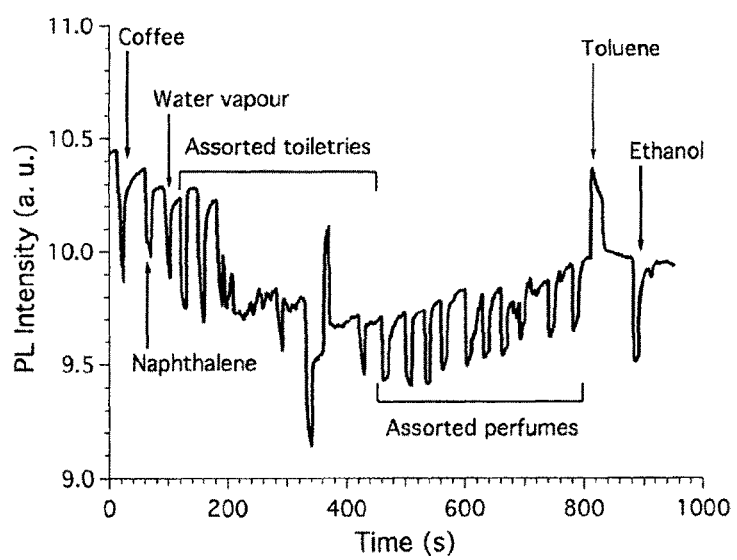
FIG. 2 is a plot of photoluminescence intensity versus time when a conventional conjugated polymer sensing device is exposed to a variety of analytes.

A conventional device containing a fluorescent conjugated polymer was found to show a ~1-2% decrease in fluorescence when exposed to a standard TNT source (not shown in FIG. 2), which is included with the device for verifying correct operation. However, when the device is exposed to a series of everyday cosmetics, chemicals, solvents etc the majority were "detected" by a decrease in the fluorescence signal. The device was exposed to the various species one at a time. The conventional device cannot readily distinguish between explosives and everyday chemicals.

Example 1

The channel of a glass capillary with the following dimensions: length=54 mm with the outside diameter=5 mm and internal diameter 0.5 mm, was coated with a triphenylamine centred thiophene-containing compound by blowing a solution of the material in toluene through the capillary with a flow of nitrogen gas. The coated capillary was then exposed sequentially to vapours of a range of everyday chemicals and nitroaromatic compounds (see FIG. 3). Vapour mixtures of species were not used. While exposure to nitroaromatic compounds results in a quenching of the fluorescence signal all the everyday chemicals give an increase in the fluorescence signal. In this way the sensing device shows selectivity.

Figure 3:
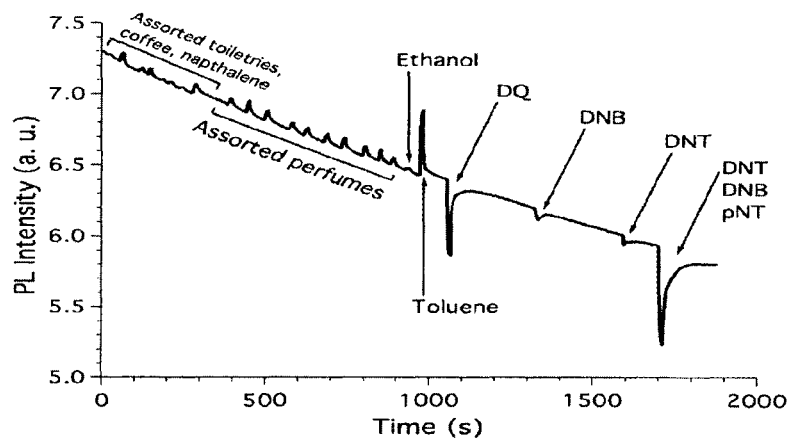
FIG. 3 is a plot of photoluminescence intensity versus time when a sensing device including the triaryl amine compound shown is exposed to a variety of analytes.
Figure 3:
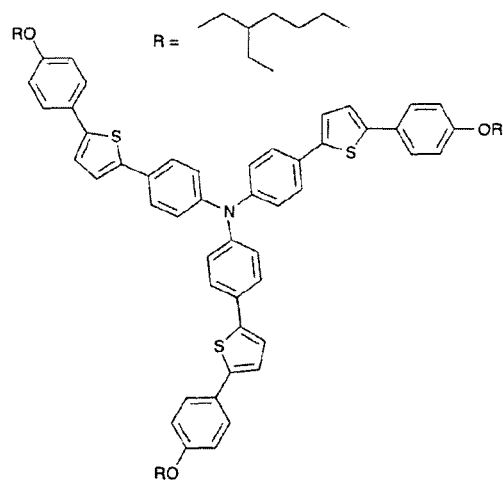

In FIG. 3 the X-axis (time) denotes the time from commencement of the experiment at which the device is exposed to a particular species.

Example 2

Figure 4:
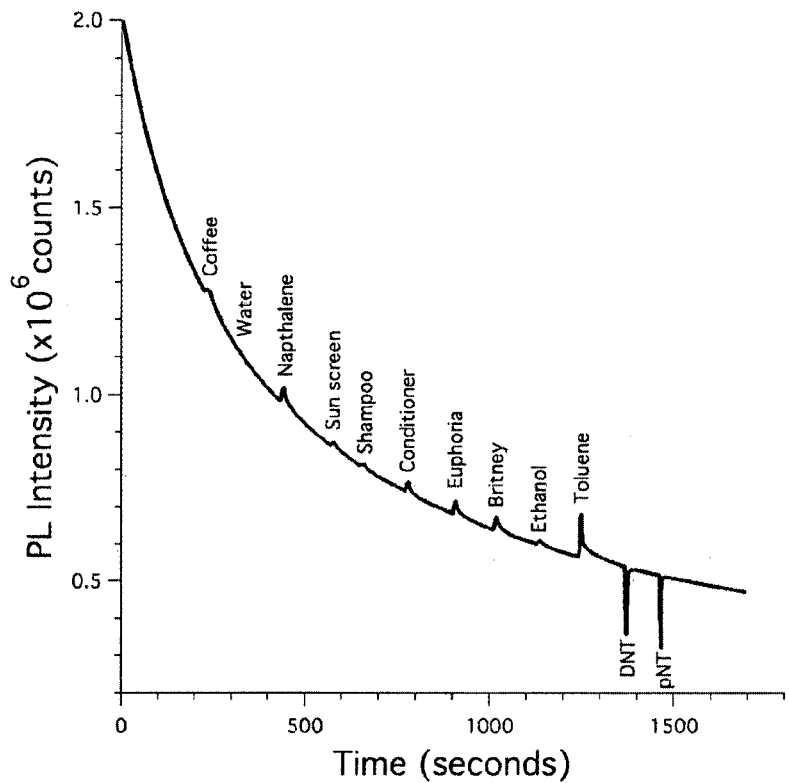
FIG. 4 is a plot of photoluminescence intensity versus time when a sensing device including the triaryl amine compound shown is exposed to a variety of analytes.
Figure 4:
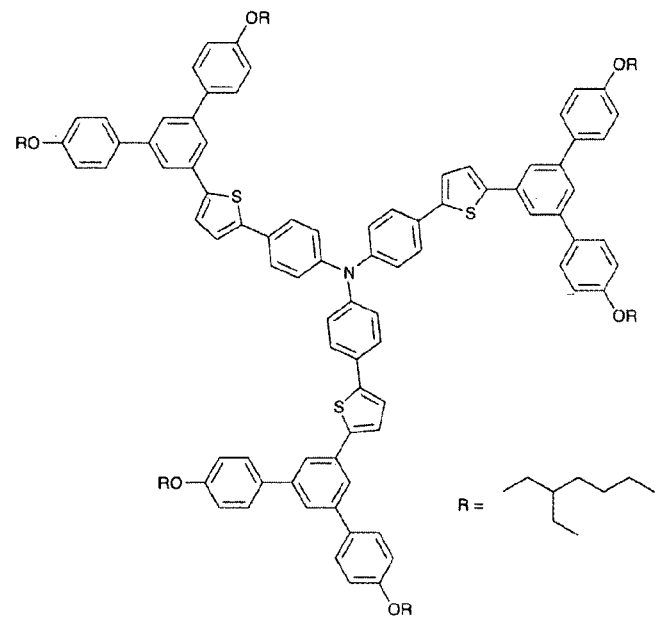

The channel of a glass capillary as above was coated with a triphenylamine centred thiophene containing dendrimer (FIG. 4) by blowing a solution of the material in toluene through the capillary with a flow of nitrogen gas. The coated capillary was then exposed sequentially to vapours of a range of everyday chemicals and nitroaromatic compounds. As with Example 1 the results show that the dendrimer exhibits an increase in fluorescence signal when exposed to the vapours from a series of everyday chemicals and quenching when it is exposed to the nitroaromatics DNT and pNT. Thus, the modification of the structure, through the addition of dendrons, has not altered the basic sensing properties.

Comparative Example 2

Figure 5:
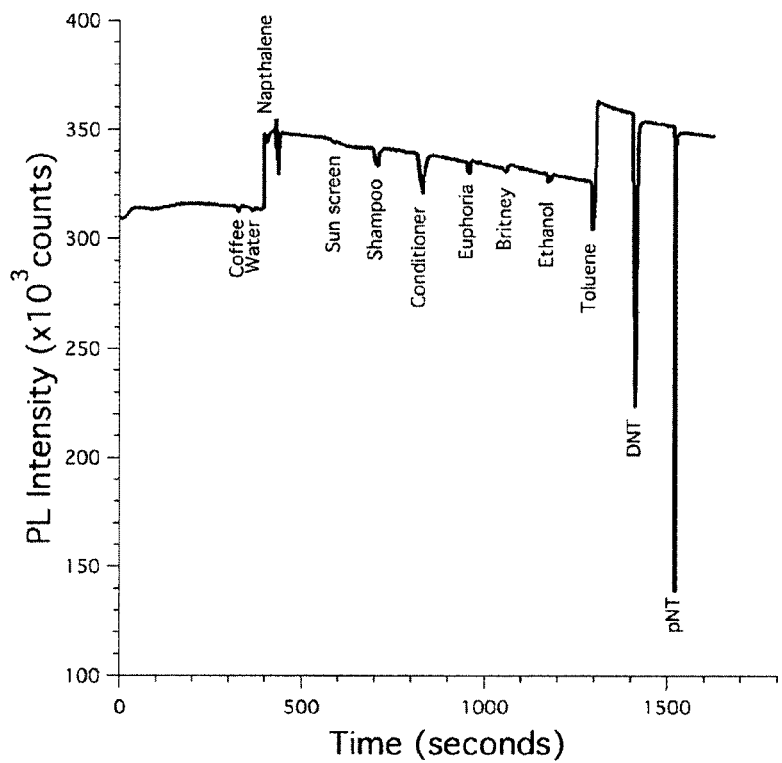
FIG. 5 is a plot of photoluminescence intensity versus time when a sensing device including a dendrimer that does not contain a triaryl amine is exposed to a variety of analytes.
Figure 5:
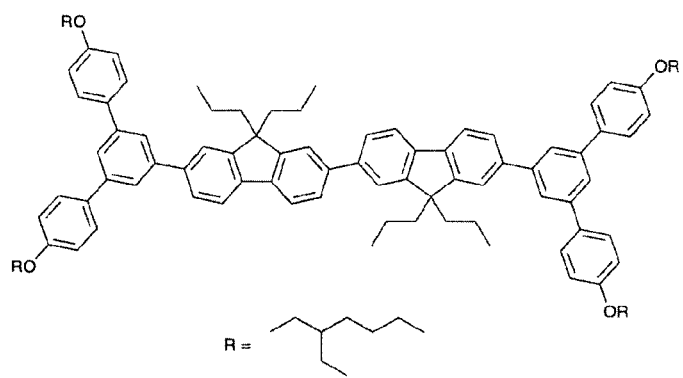

A bifluorene dendrimer, which is known to be strongly quenched by nitroaromatic vapours, was tested inside a glass capillary (same as Example 1) (see FIG. 5) to determine whether or not it featured the same selectivity observed in the triphenylamine-based compounds. The same testing procedure was followed as described for the compounds in Example 1 and 2. The fluorescence signal showed quenching responses with all of the everyday chemicals except naphthalene as well as the nitroaromatics. Toluene showed a combination of quenching/enhancement, which could be due to changes in the optical properties of the sensing film caused by swelling. This behaviour is similar to that of the original Comparative Example 1.

Example 3

Figure 6:
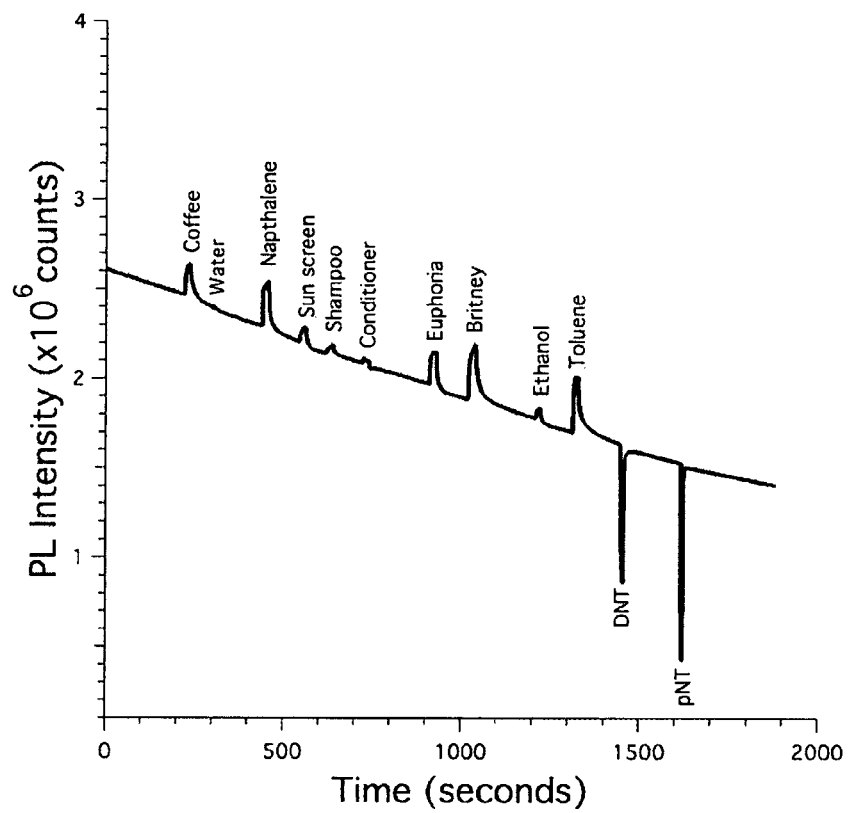
FIG. 6 is a plot of photoluminescence intensity versus time when a sensing device including the triaryl amine compound shown is exposed to a variety of analytes.
Figure 6:
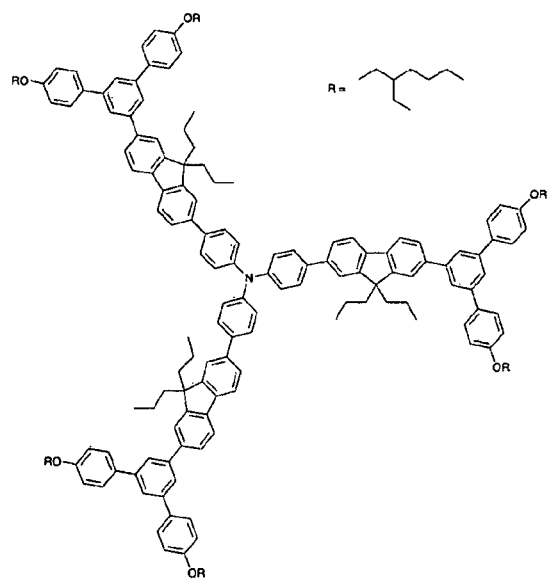

The triphenylamine centred fluorene dendrimer shown in FIG. 6 was tested to determine whether the triphenyl amine thiophene combination was necessary for the observed selectivity. Fluorene only-based compounds, such as the one described in Example 2, do not exhibit selectivity. All tests were again performed as in Examples 1, 2, and Comparative Example 2 by coating the inside of the sensing element (glass capillary with the same dimensions as Example 1) with the sensing compound. The results show the same selectivity behaviour as observed with the other triphenylamine-based compounds: only the nitroaromatic compounds show quenching of the fluorescence with everyday chemicals resulting in an increase in the fluorescence signal. The mono-fluorene compound was also found to be more stable to photooxidation than the thiophene-containing compound.

Example 4

Figure 7:
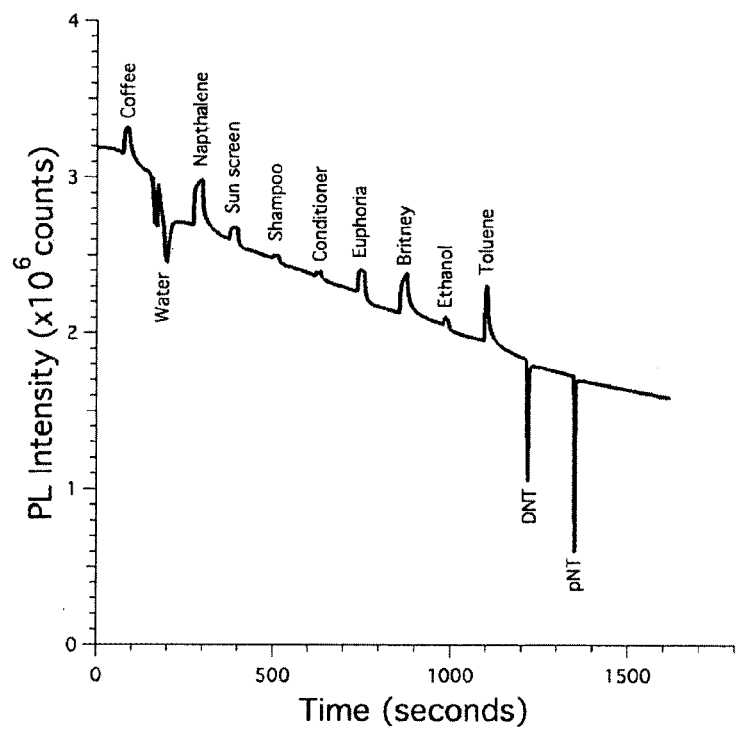
FIG. 7 is a plot of photoluminescence intensity versus time when a sensing device including the triaryl amine compound shown is exposed to a variety of analytes.
Figure 7:
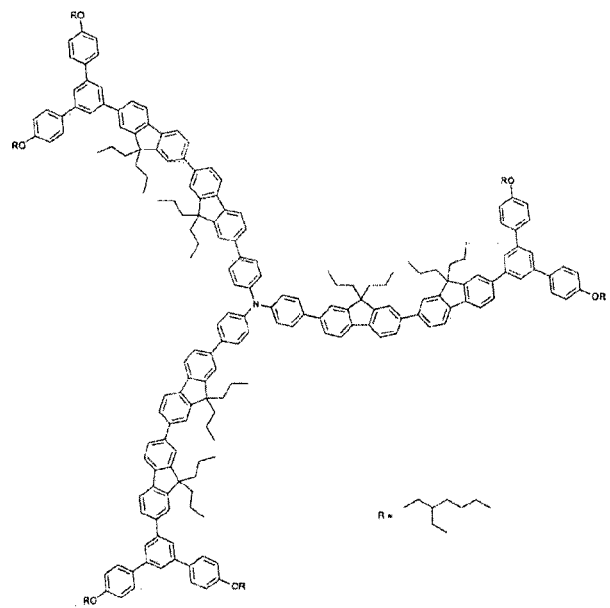

By changing the thiophene unit of the dendrimer used in Example 2 to two fluorenyl units a similar fluorescence response was seen towards a range of everyday chemicals and nitroaromatic analytes (see FIG. 7). When tested in a similar manner to the previous examples it was found that as with the mono-fluorene compound from Example 3 the photoluminescence intensity was greater and more stable than that obtained with the thiophene-containing compounds. It is important to note that all the triphenylamine compounds tested and included in the examples showed selectivity to nitroaromatic vapours.

Example 5

Synthesis of tris[4-(7-{3,5-bis[4-(2-ethylhexyloxy)phenyl]phenyl}-9,9-di-n-propylfluoren-2-yl})phenyl]amine (as Shown in FIG. 6)

A mixture of tri(4-iodophenyl)amine (93.5 mg, 0.15 mmol) (Majumdar, K. C.; Chattopadhyay, B.; Shyam, P. K.; Pal, N. Tetra. Lett. 2009, 50, 6901-6905), L3 (Jeeva, S.; Moratti, S. C. Synthesis 2007, 21, 3323-3328) (646 mg, 0.75 mmol), and tetrakis(triphenylphosphine)palladium(0) (26 mg, 0.0225 mmol), toluene (15 mL), $^t$BuOH (3 mL) and aqueous sodium carbonate (2 M, 7.5 mL) was placed under vacuum and then backfilled with $N_2$ three times before refluxing at 70° C. for 48 h. After cooling to room temperature, the layers were separated. The aqueous phase was extracted with ethyl acetate (3×50 mL), and the combined organic phases were washed with brine (2×50 mL), dried over anhydrous $MgSO_4$, filtered, and evaporated in vacuo. The residue was purified by column chromatography over silica using dichloromethane:hexane (4:10) as eluent to afford the product as light yellow solid (238 mg, 65%).

Elemental analysis (%) calcd for $C_{117}H_{207}NO_6$ C, 86.96, H, 8.54, N, 0.57; Found: C, 86.76, H, 8.40, S 0.35. $^1$H NMR (δ, 400 MHz, $CDCl_3$): 7.80-7.82 (6H, m, bpH), 7.77 (6H, J=2, d, ApH), 7.61-7.71 (32H, m, spH, FH), 7.33-7.34 (6H, br, FH), 7.03-7.06 (12H, 1/2AA'BB', spH), 3.90-3.95 (12H, m, $OCH_2$), 2.05-2.08 (12H, m, $PrCH_2$), 1.76-1.80 (6H, m, EtCH), 1.31-1.59 (48H, m, $EtCH_2$), 0.91-0.98 (36H, m, $EtCH_3$), 0.73-0.83 (30H, m, PrH). $^{13}$C NMR (δ, 400 MHz, CDCl3): 159.2, 151.8, 151.7, 146.7, 142.7, 142.1, 140.3, 140.1, 139.7, 139.5, 136.0, 133.6, 128.4, 127.9, 126.3, 125.6, 124.5, 124.4, 124.2, 121.7, 121.0, 119.9, 114.9, 70.6, 55.5, 42.9, 39.4, 30.5, 29.1, 23.9, 23.1, 17.3, 14.6, 14.1, 11.1. $\lambda_{max}$ ($CH_2Cl_2$)/nm: 376 (ε/dm$^3$ mol$^{-1}$ cm$^{-1}$: 7.6×10$^{-6}$). MS (MALDI-TOF, DCTB) Anal. Calcd for $C_{117}H_{207}NO_6$: 2443.60 (100.0%), 2444.60 (97.1%), 2445.60 (61.0%), 2442.59 (51.5%), 2446.61 (29.5%), 2447.61 (11.9%), 2448.61 (3.7%), 2445.61 (2.2%), 2446.60 (1.4%). Found: 2443.35 (100.0%), 2444.33 (97.0%), 2445.29 (60.5%), 2442.39 (48.6%), 2446.26 (30.6%), 2447.26 (11.1%), 2448.23 (5.5%). [Mt]; $T_{5\%}$ 417òC; $T_g$=106òC by DSC; $E_{1/2(Ox)}$ 0.37 V relative to the ferrocenium/ferrocene couple; PLQY (photoluminescence quantum yields) in toluene=69%.

Example 6

Synthesis of tris[4-(7-{7-[3,5-bis(4-{2-ethylhexyloxy}phenyl)phenyl]-9,9-di-n-propylfluoren-2-yl}-9,9-di-n-propylfluoren-2-yl)phenyl]amine (as Shown in FIG. 7)

A mixture of tri(4-iodophenyl)amine (63 mg, 0.1 mmol), L4 (Liedtke, A.; O'Neill, M.; Wertmoller, A.; Kitney, S. P.; Kelly, S. M. Chemistry of Materials 2008, 20, 3579-3586) (550 mg, 0.5 mmol), and tetrakis(triphenylphosphine)palladium(0) (17 mg, 0.015 mmol), toluene (15 mL), $^t$BuOH (3 mL) and aqueous sodium carbonate (2 M, 5 mL) was placed under vacuum and then backfilled with $N_2$ three times before refluxing at 70° C. for 48 h. After cooling to room temperature, the layers were separated. The aqueous phase was extracted with ethyl acetate (3×50 mL), and the combined organic phases were washed with brine (2×50 mL), dried over anhydrous $MgSO_4$, filtered, and evaporated in vacuo. The residue was purified in two steps: first, column chromatography over silica using a dichloromethane:n-hexane mixture (6:10) as eluent; and finally, the fractions were separated by chromatotron chromatography (2 mm silica plate) eluting with dichloromethane:n-hexane mixture (5:100 to 25:100) to give the compound as a light yellow solid (197 mg, 62%).

Elemental analysis (%) calcd for $C_{234}H_{267}NO_6$ C, 88.11, H, 8.44, N, 0.44; Found: C, 87.90, H, 8.68, N, 0.54. $^1$H NMR (δ, 400 MHz, $CDCl_3$): 7.76-7.80 (12H, m, FH), 7.70 (6H, J=2, d, ApH), 7.63-7.67 (44H, m, spH, FH), 7.33-7.35 (6H, J=3, d, ApH), 7.03-7.05 (12H, 1/2AA'BB', spH), 3.91-3.93 (12H, m, $OCH_2$), 2.08 (24H, m, $PrCH_2$), 1.75-1.81 (6H, m, EtCH), 1.33-1.55 (48H, m, $EtCH_2$), 0.91-0.98 (96H, m, PrH, $EtCH_3$). $^{13}$C NMR (δ, 400 MHz, $CDCl_3$): 159.2, 151.8, 151.7, 146.7, 142.6, 142.0, 140.5 140.4, 140.3, 140.0, 1139.9, 139.7, 136.1, 133.6, 128.4, 127.9, 126.2, 126.1, 125.6, 124.4, 124.2, 121.8, 121.4, 121.8, 121.4, 121.0, 120.0, 119.9, 114.9, 70.6, 55.6, 55.5, 42.9, 39.4, 30.6, 29.1, 16.9, 23.9, 23.1, 17.3, 14.6, 14.5, 11.1. $\lambda_{max}$ ($CH_2Cl_2$)/nm: 379 (ε/dm$^3$ mol$^{-1}$ cm$^{-1}$: 9.6×10$^{-6}$). MS (MALDI-TOF, DCTB) Anal. Calcd for $C_{234}H_{267}NO_6$: 3189.07 (100.0%), 3190.07 (85.7%), 3188.07 (78.0%), 3191.08 (53.4%), 3187.06 (30.4%), 3192.08 (28.0%), 3193.08 (12.0%), 3194.09 (4.0%); Found: 3189.17 (100.0%), 3188.17 (85.9%), 3190.17 (84.7%), 3191.18 (60.8%), 3187.20 (37.3%), 3192.19 (33.9%), 3193.18 (19.8%), 3194.21 (12.4%); [Mt]; $T_{5\%}$ 415òC; $T_g$=68òC by DSC; $E_{1/2(Ox)}$ 0.35 V relative to the ferrocenium/ferrocenecouple; PLQY (photoluminescence quantum yields) in toluene=79%.

Example 7

Figure 8:
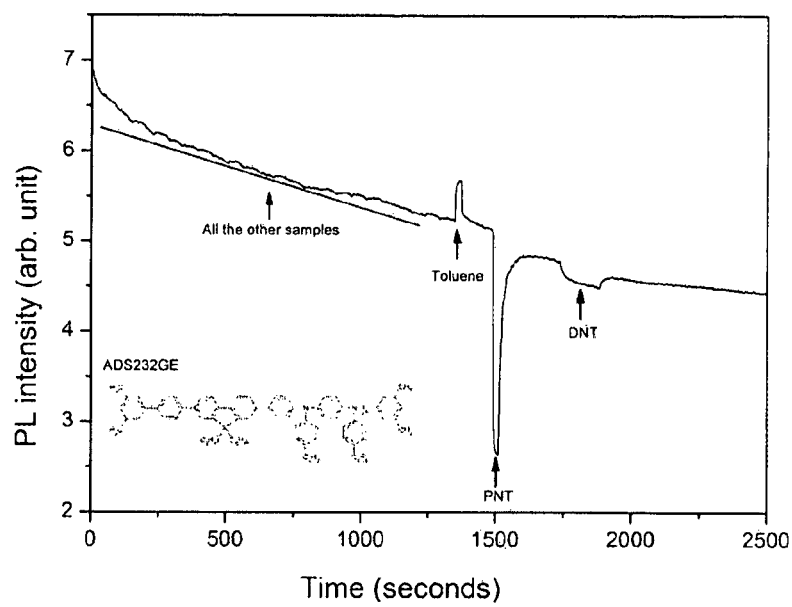
FIG. 8 is a plot of photoluminescence intensity versus time when a sensing device including the triaryl amine compound shown is exposed to a variety of analytes.
Figure 8:
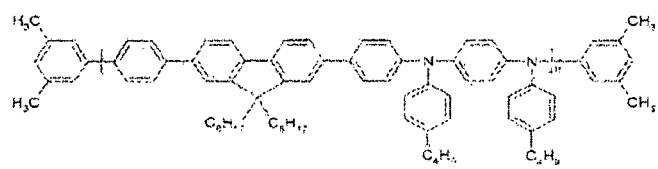

The triphenylamine-based polymer shown in FIG. 8 was tested to determine whether a triphenyl amine based polymer could be used to show the necessary selectivity. All tests were again performed in a similar manner to Example 1, 2, and Comparative Example 2 by coating the inside of the sensing element with the sensing compound. The results show the same selectivity behaviour as observed with the other triphenylamine-based compounds: only the nitroaromatic compounds show quenching of the fluorescence with everyday chemicals resulting in negligible change in the fluorescence signal. In this example there are two triphenyl amine groups per repeat unit in the polymer with them having a common phenyl group.

Example 8

Figure 9:
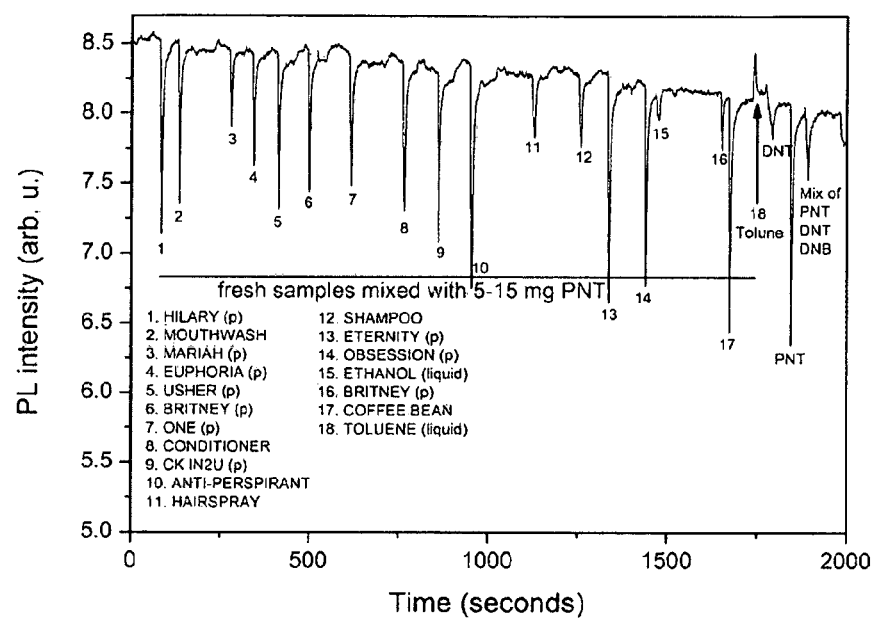
FIG. 9 is a plot of photoluminescence intensity versus time when a sensing device including the triaryl amine compound of Example 6 is exposed p-nitrotoluene (pNT) dissolved in a variety of everyday chemicals and chemical combinations.

The triphenylamine based compound from Example 6 was tested to determine whether a nitroaromatic compound (p-nitrotoluene) could be detected in the presence of other chemicals. All tests were again performed in a similar manner to Examples 1, 2, and Comparative Example 2 by coating the inside of the sensing element with the sensing compound. The results, displayed in FIG. 9, show that the p-nitrotoluene is detected with the associated responses left to right corresponding to 1 to 18 with 18 being labelled as a reference point. DNT is 2,4-dinitrotoluene, PNT is p-nitrotoluene, DNB is 1,4-dinitrobenzene and (p) denotes samples that are perfumes.

Example 9

The triphenylamine-based compound shown in FIG. 10b was tested to further confirm that compounds incorporating triphenylamine exhibit selectivity. All tests were again performed as in Examples 1, 2, and Comparative Example 2 by coating the inside of the sensing element with the sensing compound. The results shown in FIG. 10a across two plots show the same selectivity behaviour as observed with the other triphenylamine-based compounds: only the nitroaromatic compounds show quenching of the fluorescence with everyday chemicals resulting in an increase in the fluorescence signal.

Example 10

The triphenylamine-based compound shown in FIG. 11 was investigated to determine whether a molecule incorporating multiple triphenylamine units would also exhibit selectivity. Furthermore, the structure differs from many of the previous examples in that the triphenylamine is not located at the centre of the molecule but at the periphery. All tests were again performed in a similar manner to Examples 1, 2, and Comparative Example 2 by coating the inside of the sensing element (in this case a capillary with the following dimensions: length=54 mm with the outside diameter=5 mm and internal diameter=0.5 mm) with the sensing compound. The observed behaviour was consistent with the examples for the other triphenylamine-based compounds with the nitroaromatic DNT causing a decrease in the fluorescence signal and the ethanol a small increase.

Example 11

The compound shown in FIG. 12 is similar to that featured in Example 10 but with an extended chromophore though the addition of a fluorene unit. All tests were again performed in a similar manner to Examples 1, 2, and Comparative Example 2 by coating the inside of the sensing element (in this case a capillary with the following dimensions: length=54 mm with the outside diameter=5 mm and internal diameter 0.5 mm) with the sensing compound. The sensing behaviour is similar to that of the monofluorene compound in example 10 although the response and recovery of the fluorescence signal was slower.

Example 12

Synthesis of 2-bromo-7-[4-(2-ethylhexyloxy)phenyl]-9,9-di-n-propyl-9H-fluorene

2-Bromo-7-iodo-9,9-di-n-propyl-9H-fluorene (300 mg, 0.66 mmol) (Liedtke, A., O'Neill, M., Wertmoller, A., Kitney, S. P., and Kelly, S. M. Chem. Mater. 2008, 20, 3579-3586), 2-[4-(2-ethylhexyloxy)phenyl)]-4,4,5,5-tetramethyl-1,3,2-dioxaborolane (219 mg, 0.66 mmol) (Song, B. J., Song, H. M., Choi, I. T., Kim, S. K., Seo, K. D., Kang, M. S., Lee, M. J., Cho, D. W., Ju, M. J. and Kim, H. K., Chem. Eur. J., 2001, 17, 11115-11121), potassium carbonate (364 mg, 2.6 mmol), toluene (3.1 mL), $^t$BuOH (1.3 mL) and water (1.3 mL) were added to a Schlenk tube and sparged with Ar for 15 min before tetrakis(triphenylphosphine)palladium(0) (76 mg, 0.066 mmol) was added under Ar counterflow and the mixture sparged with Ar for a further 5 min. The mixture was heated at 62° C. for 3 days with vigorous stirring before being cooled with room temperature and diluted with ethyl acetate (20 mL) and water (20 mL). The organic phase was separated and washed with water (3×20 mL) and brine (50 mL), dried over anhydrous MgSO$_4$, filtered and evaporated in vacuo. The residue was purified by column chromatography over silica using hexane/ethyl acetate (1:0-49:1) as eluent, followed by chromatography using a Chromatotron apparatus over silica using hexane:dichloromethane (1:0-93:7) as eluent. This afforded the product as a viscous, colourless oil (250 mg, 71%).

$^1$H NMR ($\delta$, 400 MHz, CDCl3): 7.69-7.66 (1H, d, J=12 Hz, FlH), 7.59-7.42 (8H, m, FlH+PhH), 7.04-6.98 (2H, AA'BB', J=12 Hz, PhH), 3.91-3.89 (2H, d, J=8 Hz, OC$\underline{H}_2$), 2.00-1.90 (4H, m, PrH), 1.81-1.70 (1H, m, C$\underline{H}$(CH$_2$)$_3$), 1.31-1.59 (8H, m, EtHexC$\underline{H}_2$), 0.91-0.98 (6H, m, EtHexC$\underline{H}_3$), 0.73-0.83 (10H, m, PrH). $^{13}$C NMR ($\delta$, 100 MHz, CDCl$_3$) 159.2, 153.3, 151.2, 140.5, 140.1, 138.8, 133.9, 130.1, 128.3, 126.4, 125.9, 121.3, 121.1, 121.0, 120.2, 115.1, 70.9, 55.9, 42.9, 39.6, 30.8, 29.3, 24.1, 23.3, 17.4, 14.6, 14.3, 11.3.

Example 13

Synthesis of tris[4-(7-{4-[2-ethylhexyloxy]phenyl}-9,9-di-n-propyl-9H-fluoren-2-yl)phenyl]amine 2-Bromo-7-[4-(2-ethylhexyloxy)phenyl]-9,9-di-n-propyl-9H-fluorene (200 mg, 0.37 mmol), tris[4-(4,4,5,5-tetramethyl-1,3,2-dioxaborolan-2-yl)phenyl]amine (58 mg, 0.094 mmol) (M Nicolas, B Fabre, J. M Chapuzet, J Lessard, J Simonet, Journal of Electroanalytical Chemistry, 2000, 482, 211-216), potassium carbonate (204 mg, 1.48 mmol), tetrakis(triphenylphosphine)palladium(0) (43 mg, 0.037 mmol), $^t$BuOH (0.7 mL), water (0.7 mL) and toluene (2.1 mL) were added to a Schlenk tube and sparged with Ar for 15 min. The mixture was heated at 110° C. for 3 days with vigorous stirring before being cooled to room temperature and diluted with ethyl acetate (50 mL). The organic phase was separated and washed with water (3×50 mL) and brine (50 mL), dried over anhydrous MgSO$_4$, filtered and evaporated in vacuo. The residue was purified by chromatography using a Chromatotron apparatus over silica, eluting with dichloromethane:hexane (0:1-3:17) to afford the product as a light yellow solid (30 mg, 200).

$^1$H NMR ($\delta$, 300 MHz, CDCl$_3$) 7.77-7.73 (6H, m, PhH), 7.65-7.53 (24H, m, FlH+PhH), 7.03-7.00 (6H, d, J=11 Hz), 3.92-3.90 (6H, d, J=6 Hz, OC$\underline{H}_2$), 2.07-2.04 (12H, m, PrH), 1.82-1.76 (3H, m, C$\underline{H}$(CH$_2$)$_3$), 1.60-1.35 (24H, m, EtHexC$\underline{H}_2$), 1.00-0.92 (18H, m, EtHexC$\underline{H}_3$), 0.83-0.70 (30H, m, PrH); Anal. Calcd for C$_{117}$H$_{135}$NO$_3$: 1603.05 (100.00%), 1602.04 (78.0%), 1604.05 (64.0%), 1605.05 (26.5%), 1606.06 (8.7%), 1607.06 (2.2%), 1605.06 (1.0%). Found: 1602.65 (100.0%), 1601.70 (82.9%), 1603.63 (72.2%), 1604.58 (32.2%), 1605.55 (7.2%), 1606.61 (3.1%).

Example 14

Synthesis of 7-bromo-7'-[4-(2-ethylhexyloxy)phenyl]-9,9,9',9'-tetra-n-propyl-9H,9'H-2,2'-bifluorene 7-Bromo-7'-iodo-9,9,9',9'-tetra-n-propyl-9H,9'H-2,2'-bifluorene (500 mg, 0.71 mmol) (Cavaye, H.; Shaw, P. E.;

Wang, X.; Burn, P. L.; Lo, S.-C.; Meredith, P. Macromolecules 2010, 43, 10253-10261), 2-[4-(2-ethylhexyloxy)phenyl]-4,4,5,5-tetramethyl-1,3,2-dioxaborolane (236 mg, 0.71 mmol) (Song, B. J., Song, H. M., Choi, I. T., Kim, S. K., Seo, K. D., Kang, M. S., Lee, M. J., Cho, D. W., Ju, M. J. and Kim, H. K., Chem. Eur. J., 2001, 17, 11115-11121), potassium carbonate (392 mg, 2.8 mmol), toluene (4.2 mL), $^t$BuOH (1.4 mL) and water (1.4 mL) were added to a Schlenk tube then sparged with Ar for 15 min. Tetrakis(triphenylphosphine)palladium(0) (82 mg, 0.071 mmol) was then added under Ar counterflow and the mixture sparged with Ar for a further 5 min before the mixture was then heated at 62° C. for 3 days with vigorous stirring. After this time the reaction was cooled to room temperature and diluted with ethyl acetate (50 mL) and water (50 mL). The organic phase was separated and washed with water (3×30 mL) and brine (50 mL), dried over anhydrous MgSO$_4$, filtered and evaporated in vacuo. The residue was purified by column chromatography over silica using hexane:ethyl acetate (96:4) as eluent, followed by chromatography using a Chromatotron apparatus over silica using hexane:dichloromethane (0:1-9:1) as eluent. This afforded the product as a colourless solid (127 mg, 23%).

$^1$H NMR (δ, 400 MHz, CDCl3): 7.79-7.73 (3H, m, FlH), 7.66-7.46 (11H, m, FlH+PhH), 7.04-6.98 (2H, AA'BB', J=12 Hz, PhH), 3.92-3.90 (2H, d, J=8 Hz, OC$\underline{H}_2$), 2.08-1.94 (8H, m, PrH), 1.80-1.73 (1H, m, C$\underline{H}$(CH$_2$)$_3$), 1.58-1.30 (8H, m, EtHexC$\underline{H}_2$), 0.91-0.98 (6H, m, EtHexC$\underline{H}_3$), 0.73-0.83 (20H, m, PrH). $^{13}$C NMR (δ, 100 MHz, CDCl$_3$) 159.1, 153.4, 151.9, 151.8, 151.3, 141.2, 140.4, 140.2, 140.1, 140.0, 139.5, 139.3, 134.1, 130.2, 128.3, 126.5, 126.5, 126.4, 126.3, 125.8, 121.5, 121.3, 121.2, 121.2, 121.1, 120.2, 120.1, 120.0, 115.0, 70.8, 55.9, 55.7, 43.0, 42.9, 39.6, 30.7, 29.3, 24.1, 23.3, 17.5, 17.4, 14.7, 14.6, 14.3, 11.3

Example 15

Synthesis of tris[4-(7'-{4-[2-ethylhexyloxy]phenyl}-9,9,9',9'-tetra-n-propyl-9H,9'H-[2,2'-bifluoren]-7-yl)phenyl]amine (Structure Shown in FIG. 10b)

7-Bromo-7'-[4-(2-ethylhexyloxy)phenyl]-9,9,9',9'-tetra-n-propyl-9H,9'H-2,2'-bifluorene (400 mg, 0.51 mmol), tris[4-(4,4,5,5-tetramethyl-1,3,2-dioxaborolan-2-yl)phenyl]amine (64 mg, 0.01 mmol) (M Nicolas, B Fabre, J. M Chapuzet, J Lessard, J Simonet, Journal of Electroanalytical Chemistry, 2000, 482, 211-216), tri(o-tolyl)phosphine (18 mg, 0.06 mmol), palladium(II) acetate (3.4 mg, 0.015 mmol), tetra-n-butylammonium bromide (80 mg, 0.25 mmol), potassium phosphate (433 mg, 2.04 mmol), toluene (2 mL) and water (0.5 mL) were added to a Schlenk tube and sparged with Ar for 15 min before being heated at 100° C. for 3 days with vigorous stirring. After this time the reaction was cooled to room temperature and diluted with ethyl acetate (20 mL). The organic phase was separated and washed with water (4×50 mL) and brine (50 mL), dried over anhydrous MgSO$_4$, filtered and evaporated in vacuo. The residue was purified by column chromatography over silica using hexane:ethyl acetate (97:3) as the eluent, followed by chromatography using a Chromatotron apparatus over silica using hexane:dichloromethane (0:1-9:1) as eluent. This afforded the product as a light yellow solid (32 mg, 28%).

$^1$H NMR (δ, 400 MHz, CDCl3): 7.82-7.76 (12H, m, FlH), 7.68-7.55 (36H, m, FlH+PhH), 7.35-7.33 (6H, d, J=8 Hz, PhH), 7.03-7.01 (6H, AA'BB', J=8 Hz, PhH), 3.92-3.91 (6H, d, J=4 Hz, OC$\underline{H}_2$), 2.11-2.04 (24H, m, PrH), 1.79-1.73 (3H, m, C$\underline{H}$(CH$_2$)$_3$), 1.57-1.34 (24H, m, EtHexC$\underline{H}_2$), 0.98-0.91 (18H, m EtHexC$\underline{H}_3$), 0.86-0.70 (60H, m, PrH); Anal. Calcd. For C$_{174}$H$_{195}$NO$_3$: 2347.52 (100.0%), 2348.52 (95.1%), 2349.52 (58.4%), 2346.51 (52.5%), 2350.53 (27.9%) Found: 2347.26 (100.0%), 2348.27 (99.3%), 2349.27 (69.5%), 2346.26 (54.2%), 2350.25 (41.1%).

Example 16

Synthesis of 2,7-bis[4,4'-N,N-diphenylaniline]-9,9-di-n-propylfluorene (Structure Shown in FIG. 11)

A mixture of 4-(N,N-diphenylamino)phenylboronic acid (1.05 g, 3.60 mmol) (Li, Z. H.; Wong, M. S. Org. Lett. 2006, 8, 1499-1502), 2,7-dibromo-9,9-di-n-propylfluorene (490 mg, 1.20 mmol) (Aldred, M. P.; Hudson, R.; Kitney, S. P.; Vlachos, P.; Liedtke, A.; Woon, K. L.; O'Neill, M.; Kelly, S. M. Liquid Crystals 2008, 35, 413-427), and tetrakis(triphenylphosphine)palladium(0) (139 mg, 0.12 mmol), tetrahydrofuran (15 mL) and aqueous sodium carbonate (2 M, 4 mL) was placed under vacuum and then backfilled with argon three times before heating at 80° C. for 48 h. After cooling to room temperature, the layers were separated. The aqueous phase was extracted with dichloromethane (10×50 mL), and the combined organic phases were washed with brine (2×100 mL), dried over anhydrous Na$_2$SO$_4$, filtered, and evaporated in vacuo. The residue was purified by column chromatography over silica using toluene:petrol ether (1:3) as eluent to afford the product as a light white solid (610 mg, 69%).

Elemental analysis (%) calcd for C$_{55}$H$_{48}$N$_2$ C, 89.63, H, 6.56, N, 3.80; Found: C, 89.28, H, 6.60, N, 3.69. $^1$H NMR (δ, 500 MHz, CDCl$_3$): 7.73-7.7.74 (2H, in, FlH), 7.55-7.58 (8H, m, FlH+TpaH), 7.27-7.30 (8H, m, TpaH), 7.14-7.19 (12H, m, TpaH), 7.03-7.06 (4H, m, TpaH), 2.00-2.03 (4H, m, PrH), 0.73-0.80 (4H, m, PrH), 0.67-0.70 (6H, m, PrH). $^{13}$C NMR (δ, 125 MHz, CDCl$_3$): 151.6, 147.7, 147.0, 139.7, 139.4, 135.6, 129.3, 127.8, 125.5, 124.3, 124.1, 122.9, 120.9, 119.9, 55.4, 42.9, 17.3, 14.5.

Example 17

Synthesis of 7,7'-bis[4,4'-bis(N,N-diphenylaniline)]-9,9,9',9'-tetra-n-propyl-9H,9'H-2,2'-bifluorene (Structure Shown in FIG. 12)

A mixture of 4-(N,N-diphenylamino)phenylboronic acid (1.15 g, 4.00 mmol) (Li, Z. H.; Wong, M. S. Org. Lett. 2006, 8, 1499-1502), 7,7'-dibromo-9,9,9',9'-tetra-n-propyl-2,2'-bifluorene (871 mg, 1.33 mmol) (Kelley, C. J.; Ghioghis, A.; Qin, Y.; Kauffman, J. M.; Novinski, J. A.; Boyko, W. J. J. Chem. Res., Miniprint 1999, 0401-0418), and tetrakis(triphenylphosphine)palladium(0) (153 mg, 0.13 mmol), tetrahydrofuran (15 mL) and aqueous sodium carbonate (2 M, 4 mL) was placed under vacuum and then backfilled with argon three times before refluxing at 80° C. for 48 h. After cooling to room temperature, the layers were separated. The aqueous phase was extracted with ethyl acetate (4×50 mL) and dichloromethane (3×50 mL), and the combined organic phases were washed with brine (2×100 mL), dried over anhydrous Na$_2$SO$_4$, filtered, and evaporated in vacuo. The residue was purified by column chromatography over silica using toluene:petrol ether (1:3) as eluent to afford the product as a light white solid (722 mg, 55%).

Elemental analysis (%) calcd for C$_{74}$H$_{68}$N$_2$ C, 90.20, H, 6.96, N, 2.84; Found: C, 90.13, H, 7.02, N, 2.78. $^1$H NMR (δ, 500 MHz, CDCl$_3$): 7.76-7.7.80 (4H, m, Fl), 7.64-7.68 (4H, m, FlH), 7.57-7.60 (8H, m, FlH+TpaH), 7.26-7.31 (8H, m, TpaH), 7.15-7.21 (12H, m, TpaH), 7.03-7.07 (4H, m, TpaH), 2.05-2.09 (8H, m, PrH), 0.77-0.84 (8H, m, PrH), 0.70-0.74 (12H, m, PrH). $^{13}$C NMR (δ, 100 MHz, CDCl$_3$): 151.71, 151.68, 147.7, 147.1, 140.4, 140.0, 139.7, 139.5, 135.6, 129.3, 127.8, 126.1, 125.5, 124.4, 124.0, 122.9, 121.3, 121.0, 120.0, 119.9, 55.5, 42.9, 17.3, 14.6.

Example 18

The triphenylamine-based compound shown in FIG. 13 was tested to further confirm that compounds incorporating triphenylamine exhibit selectivity. All tests were again performed in a similar manner to Examples 1, 2, and Comparative Example 2 by coating the inside of the sensing element with the sensing compound. The results are consistent with the examples for the other triphenylamine-based compounds with the nitroaromatic DNT causing a decrease in the fluorescence signal and the ethanol a small increase.

The invention claimed is:

1. A sensing element for use in the detection of an analyte based on a luminescent response wherein the sensing element is configured to provide improved detection selectivity and sensitivity with respect to explosives and explosive-related analytes, the sensing element comprising a luminescent triaryl amine compound provided as a coating on a substrate, wherein the triaryl amine compound is represented by formula (Id) or formula (Ie):

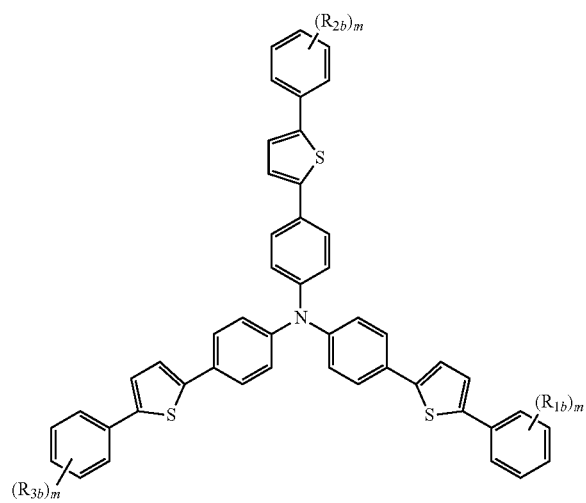
(Id)

in which m at each occurrence is independently 1 or 2, $R_{1b}$, $R_{2b}$ and $R_{3b}$ are independently selected from $C_1$-$C_{20}$ alkyl, or $C_1$-$C_{20}$ alkoxy when m is 1, and when m is 2, $R_{1b}$, $R_{2b}$ and $R_{3b}$ are independently substituted phenyls; or

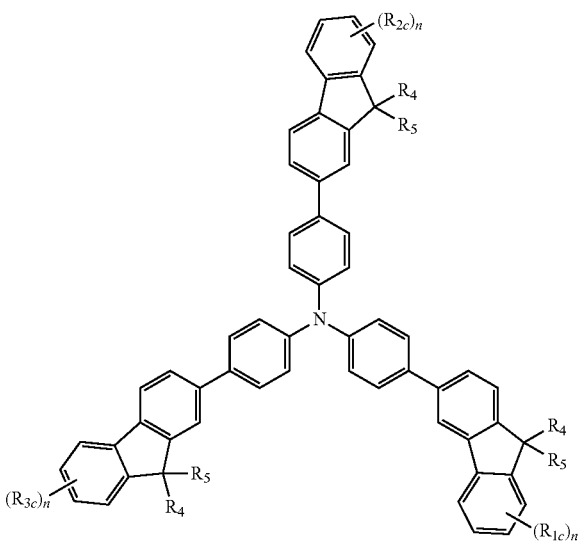
(Ie)

in which $R_{1c}$, $R_{2c}$ and $R_{3c}$ are independently selected from a substituted aryl, or a substituted heteroaryl, n at each occurrence is independently 1, 2, or 3, and $R_4$ and $R_5$ at each occurrence is independently $C_1$-$C_{10}$ alkyl, $C_1$-$C_{10}$ alkoxy, glycols of differing lengths, and crosslinkable groups such as vinyl, methacrylate or oxetanes attached via a flexible chain.

2. A sensing element according to claim 1, wherein the coating has a thickness of up to 100 nm.

3. A sensing element according to claim 1, wherein the coating is provided on the internal surface of a capillary tube.

4. A sensing element according to claim 3, wherein the capillary tube has an internal diameter of from 100 μm to 1 mm and a length of up to 100 mm.

5. A sensor device for the detection of an analyte based on luminescent response, the sensor device comprising a sensing element as claimed in claim 1.

6. A sensor device according to claim 5, comprising an excitation source to supply electromagnetic radiation that interacts with the triaryl amine compound, a light detector for receiving light from the triaryl amine compound, a component that allows the output of the light detector to be visualized or otherwise represented for interpretation and one or more temperature control elements for regulating and detecting the temperature of parts of the device.

7. A method of detecting an analyte wherein the method provides improved detection selectivity and sensitivity with respect to explosives and explosive-related analytes, which method comprises:

(i) allowing a luminescent compound comprising a triaryl amine moiety to interact with the analyte and measuring the luminescent properties of the compound in the presence of the analyte, the luminescent compound being provided as a coating on a substrate, wherein the compound is represented by formula (Id) or formula (Ie):

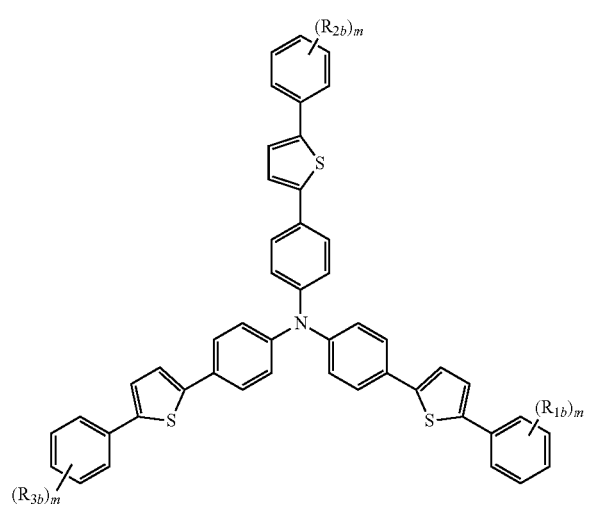

in which m at each occurrence is independently 1 or 2, $R_{1b}$, $R_{2b}$ and $R_{3b}$ are independently selected from $C_1$-$C_{20}$ alkyl, or $C_1$-$C_{20}$ alkoxy when m is 1, and when m is 2, $R_{1b}$, $R_{2b}$ and $R_{3b}$ are independently substituted phenyls; or

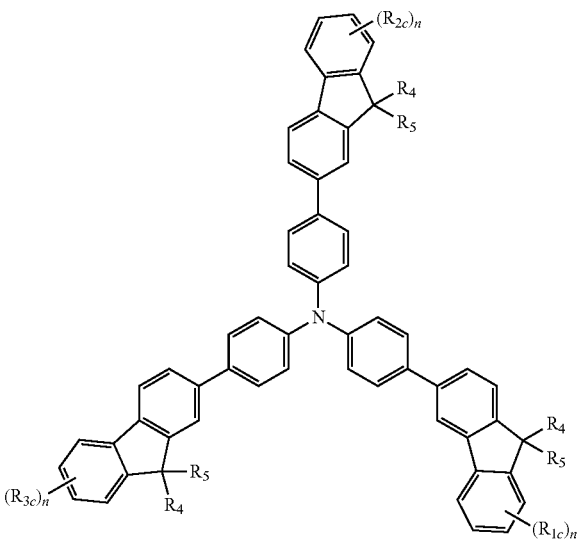

in which $R_{1c}$, $R_{2c}$ and $R_{3c}$ are independently selected from a substituted aryl, or a substituted heteroaryl, n at each occurrence is independently 1, 2, or 3, and $R_4$ and $R_5$ at each occurrence is independently $C_1$-$C_{10}$ alkyl, $C_1$-$C_{10}$ alkoxy, glycols of differing lengths, and cross-linkable groups such as vinyl, methacrylate or oxetanes attached via a flexible chain;

(ii) detecting a difference between the luminescent properties measured in step (i) and the luminescent properties of the compound prior to measurement of luminescent properties in step (i); and (iii) determining whether the analyte is present based on the difference in luminescent properties detected in step (ii).

8. A method according to claim 7, comprising:

(a) exciting the luminescent compound comprising a triaryl amine moiety and measuring the luminescent properties of the compound;

(b) allowing the compound to interact with the analyte and measuring the luminescent properties of the compound in the presence of the analyte;

(c) detecting a difference between the luminescent properties measured in steps (a) and (b); and (d) determining whether the analyte is present based on the difference in luminescent properties detected in step (c).

9. The sensing element according to claim 1 wherein the compound of formula (Id) is represented by the following formula:

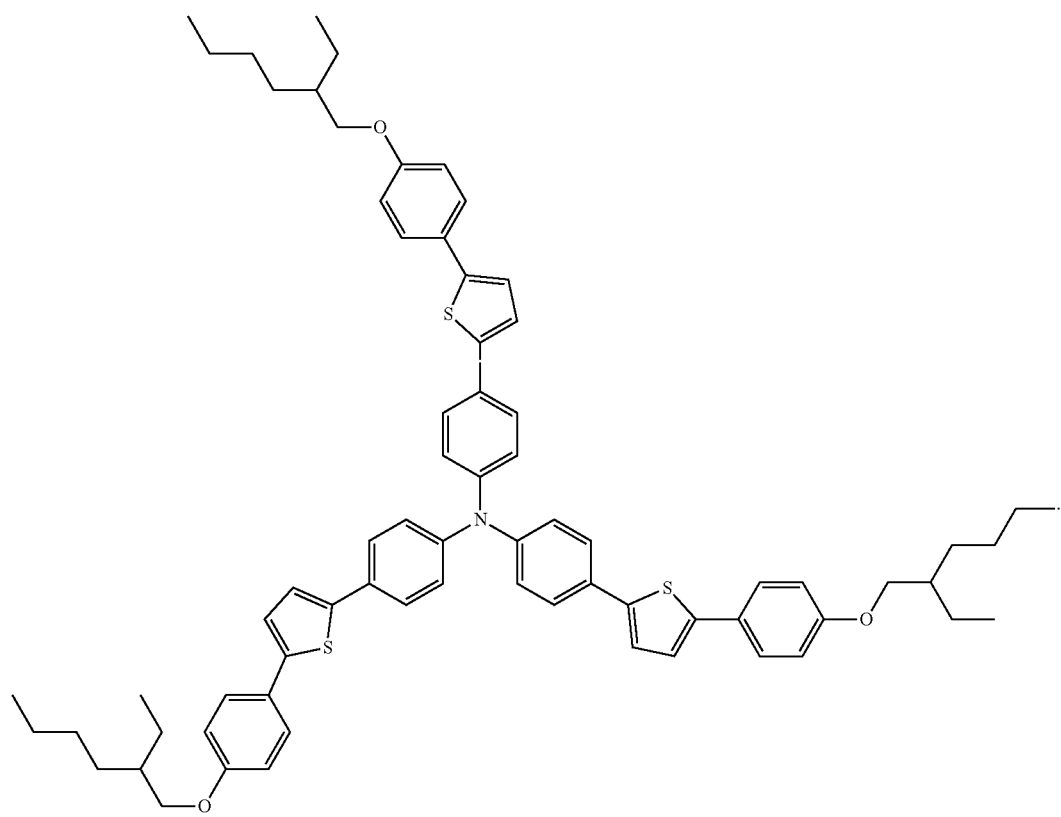
10. The sensing element according to claim 1 wherein the compound of formula (Id) is represented by the following formula:
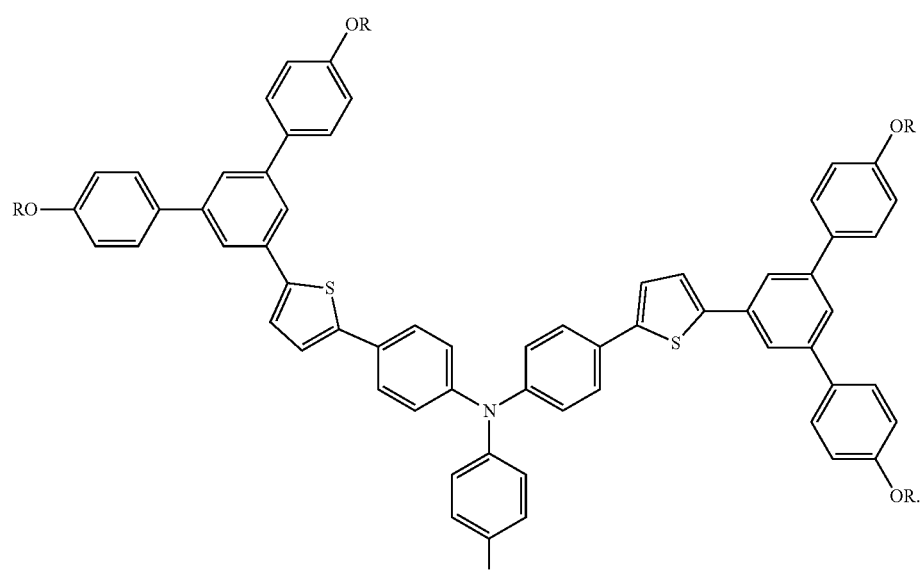

-continued

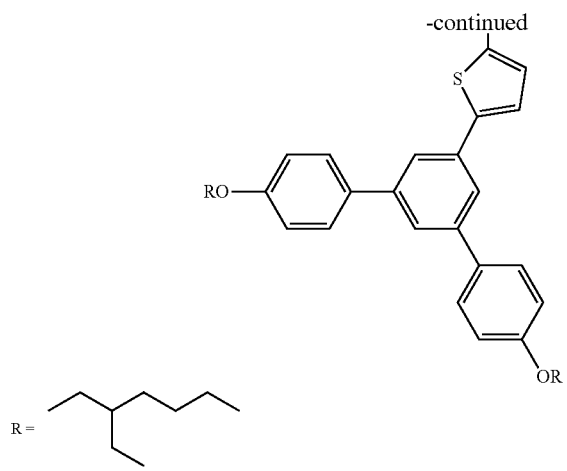

11. The sensing element according to claim 1 wherein the compound of formula (Ie) is a compound of formula (Ig):

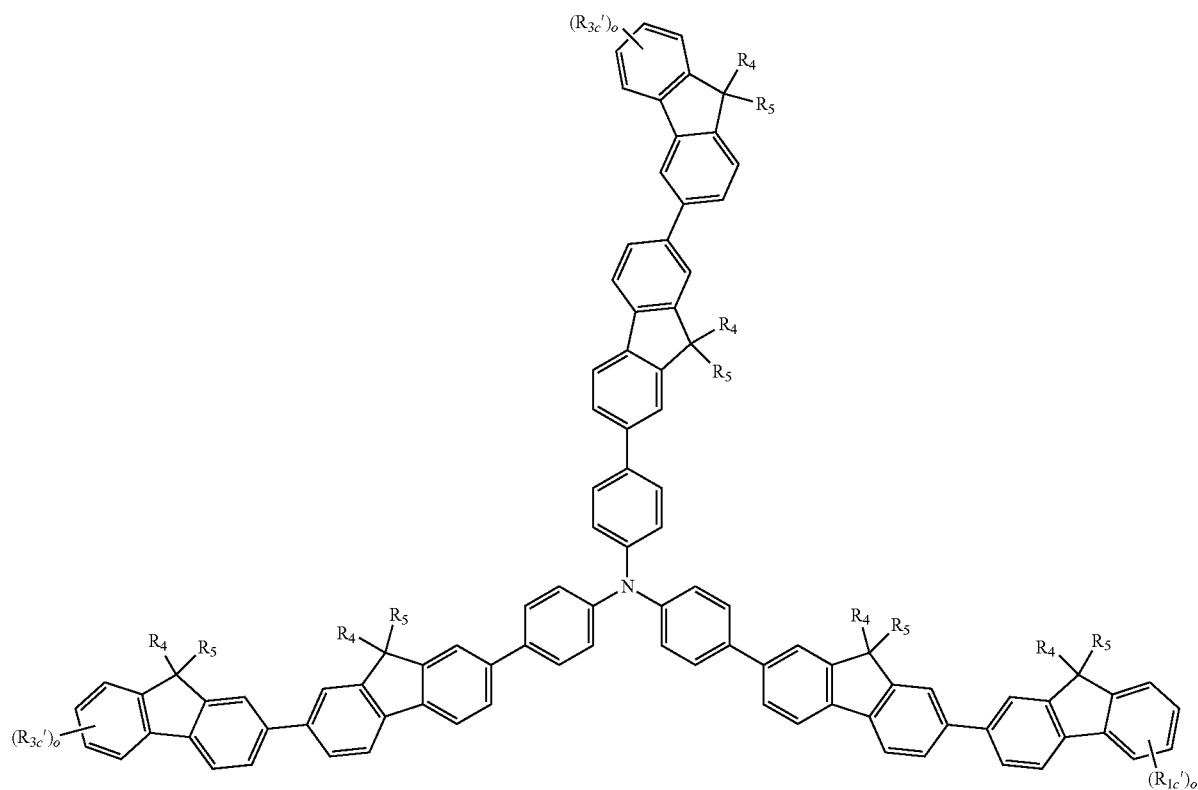

in which $R_{1c}'$, $R_{2c}'$ and $R_{3c}'$ are independently selected from a substituted aryl or a substituted heteroaryl; o at each occurrence is independently 1, 2, or 3; and $R_4$ and $R_5$ at each occurrence is independently $C_1$-$C_{10}$ alkyl, $C_1$-$C_{10}$ alkoxy, glycols of differing lengths, and cross-linkable groups such as vinyl, methacrylate or oxetanes attached via a flexible chain.

12. The sensing element according to claim 1 wherein the compound of formula (Ie) is tris[4-(7-{3,5-bis[4-(2-ethylhexyloxy)phenyl]phenyl}-9,9-di-n-propylfluoren-2-yl})-phenyl]amine:
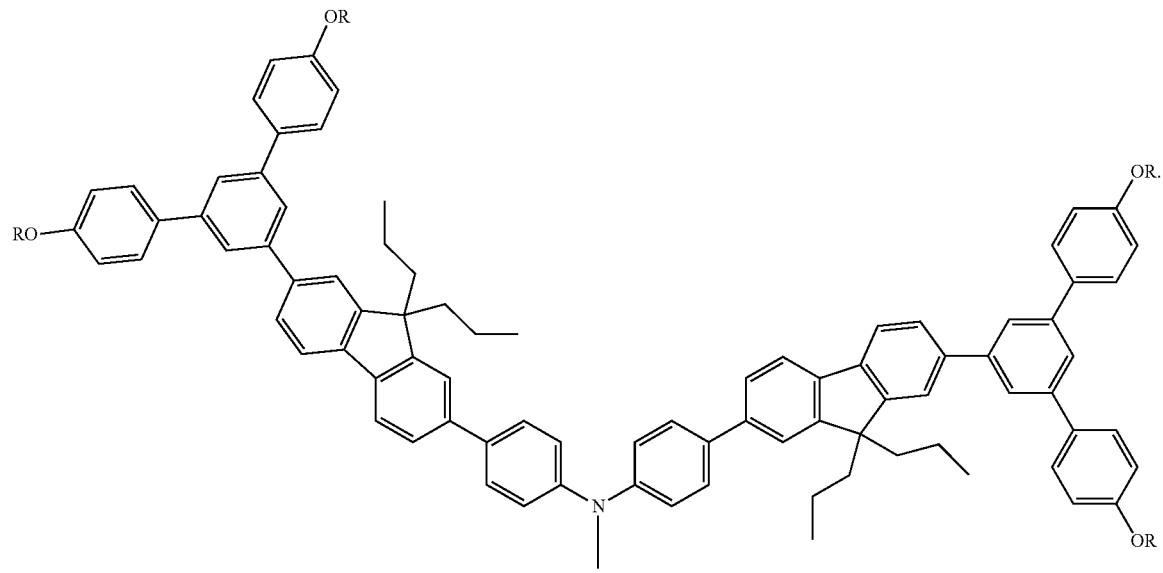
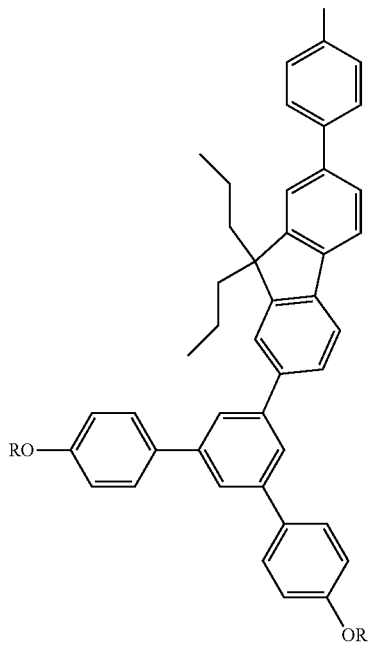
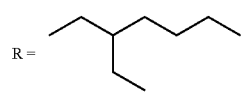

13. The sensing element according to claim 1 wherein the compound of formula (Ie) is tris[4-(7-{7-[3,5-bis(4-{2-ethylhexyloxy}phenyl)phenyl]-9,9-di-n-propylfluoren-2-yl}-9,9-di-n-propylfluoren-2-yl)phenyl]amine:
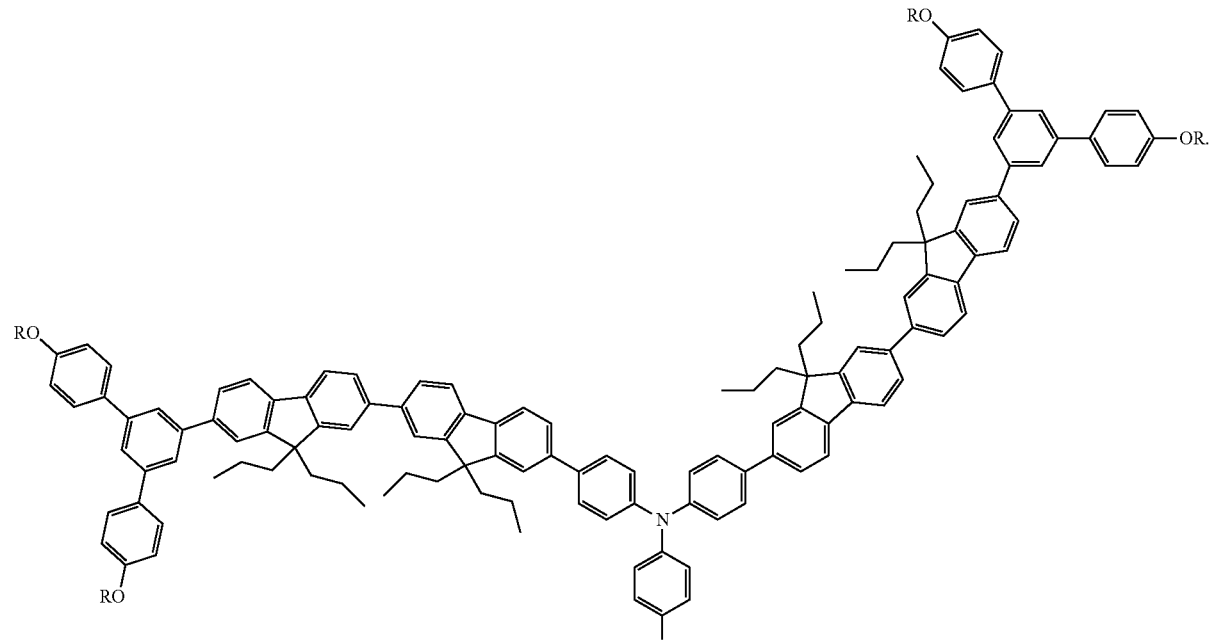
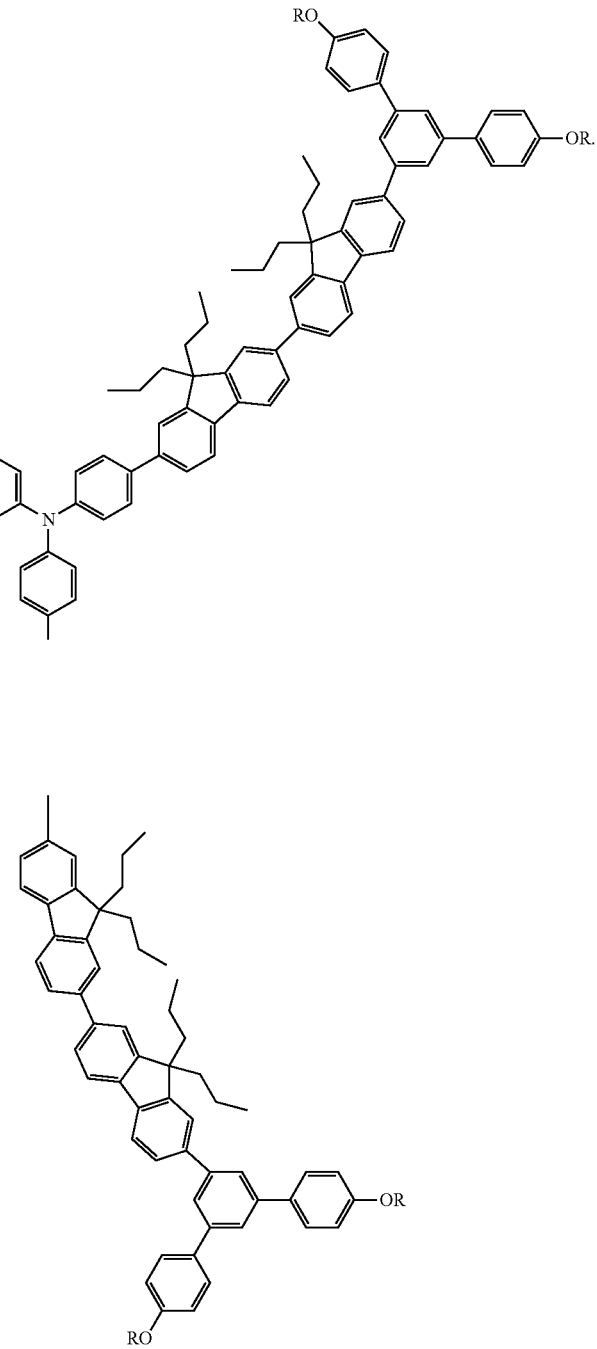
R = 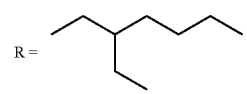

14. The method according to claim 7 wherein the compound of formula (Id) is represented by the following formula:
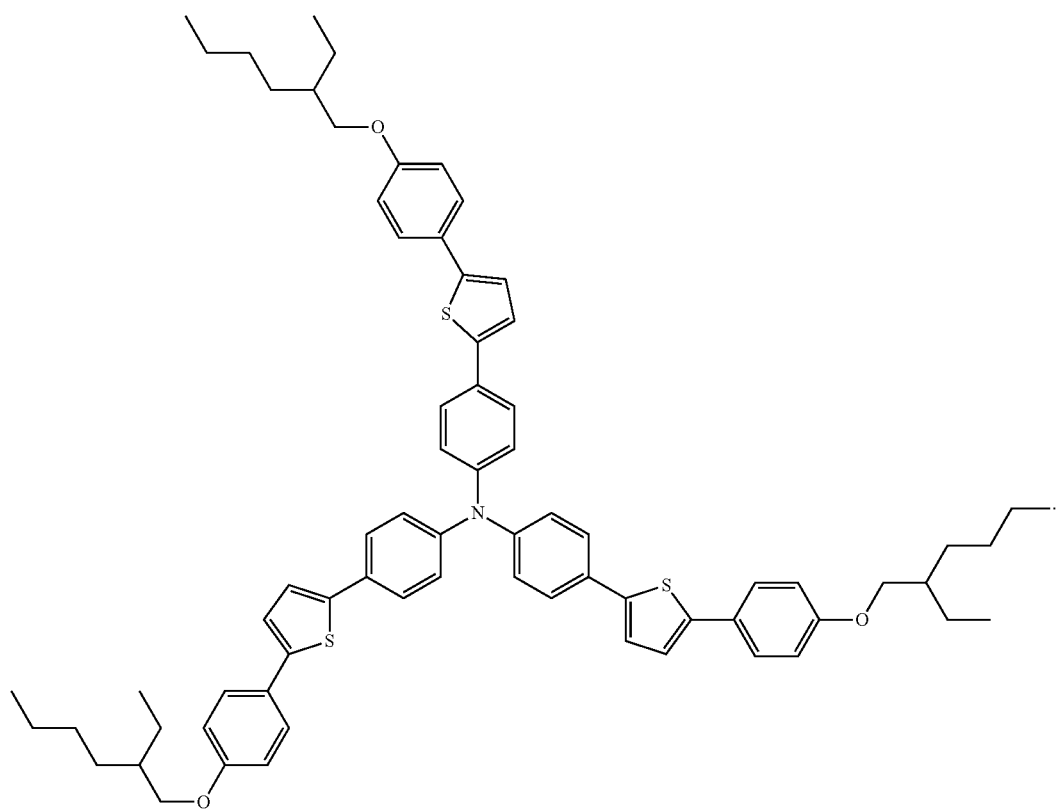
15. The method according to claim 7 wherein the compound of formula (Id) is represented by the following formula:

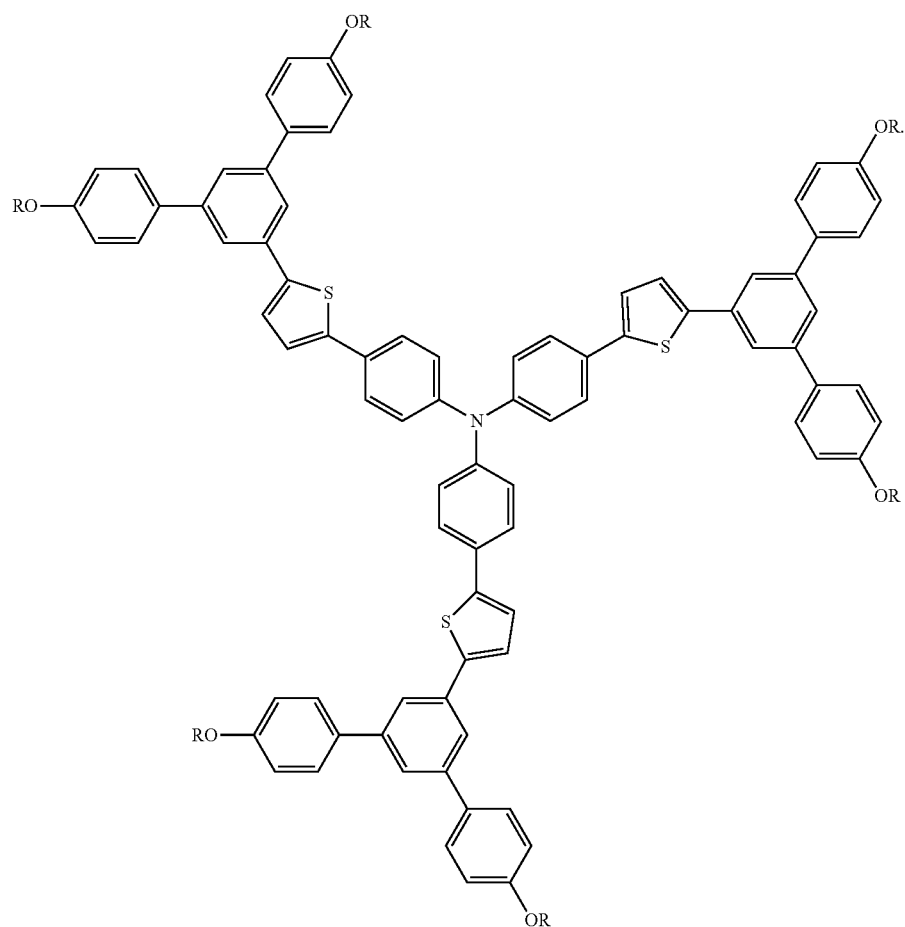
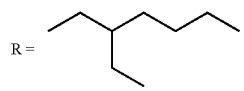
16. The method according to claim 7 wherein the compound of formula (Ie) is a compound of Formula (Ig):
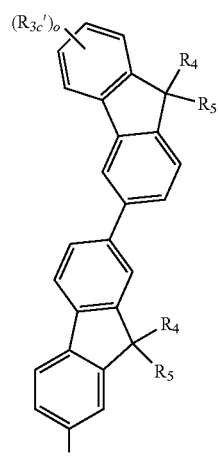

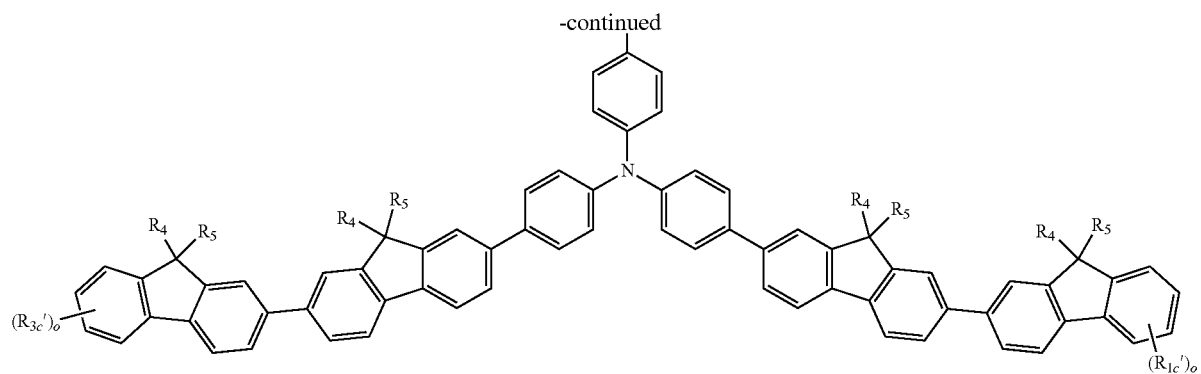

in which $R_{1c}'$, $R_{2c}'$ and $R_{3c}'$ are independently selected from a substituted aryl or a substituted heteroaryl; o at each occurrence is independently 1, 2, or 3; and $R_4$ and $R_5$ at each occurrence is independently $C_1$-$C_{10}$ alkyl, $C_1$-$C_{10}$ alkoxy, glycols of differing lengths, and cross-linkable groups such as vinyl, methacrylate or oxetanes attached via a flexible chain.

17. The method according to claim 7 wherein the compound of formula (Ie) is tris[4-(7-{3,5-bis[4-(2-ethylhexyloxy)phenyl]phenyl}-9,9-di-n-propylfluoren-2-yl})-phenyl]amine

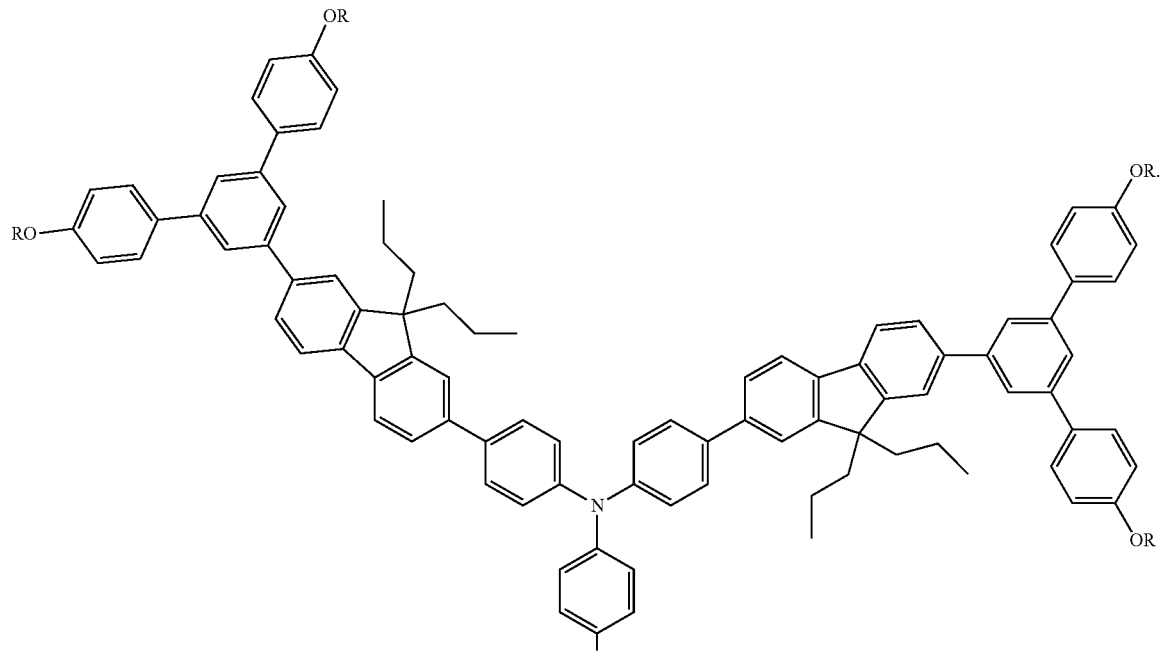

-continued
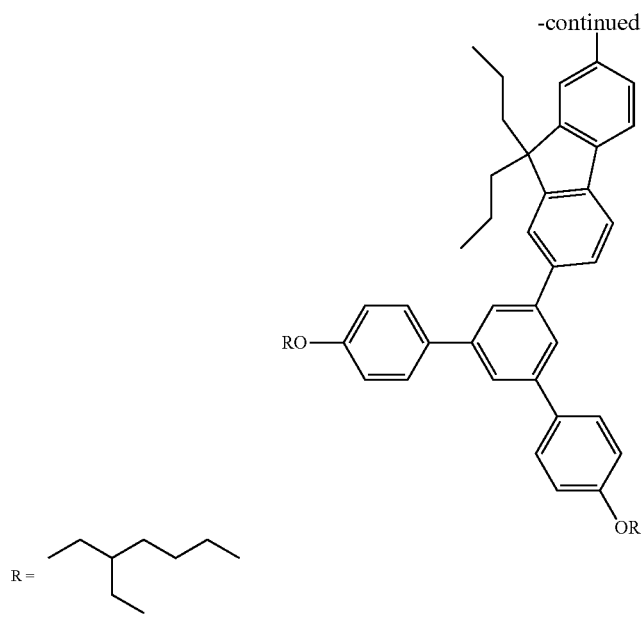
25
18. The method according to claim 7 wherein the compound of formula (Ie) is tris[4-(7-{7-[3,5-bis(4-{2-ethylhexyloxy}phenyl)phenyl]-9,9-di-n-propylfluoren-2-yl}-9,9-di-n-propylfluoren-2-yl)phenyl]amine.
* * * * *